US012702384B2

(12) United States Patent
Winkler Brown et al.

(10) Patent No.: US 12,702,384 B2
(45) Date of Patent: Aug. 11, 2026

(54) PREVIEW OF INTRALUMINAL ULTRASOUND IMAGE ALONG LONGITUDINAL VIEW OF BODY LUMEN

(71) Applicant: PHILIPS IMAGE GUIDED THERAPY CORPORATION, San Diego, CA (US)

(72) Inventors: Emily Winkler Brown, Amsterdam (NL); Ronald Christiaan Helmstrijd, Best (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 73 days.

(21) Appl. No.: 18/290,312

(22) PCT Filed: Apr. 7, 2022

(86) PCT No.: PCT/EP2022/059316
§ 371 (c)(1),
(2) Date: Nov. 13, 2023

(87) PCT Pub. No.: WO2022/238058
PCT Pub. Date: Nov. 17, 2022

(65) Prior Publication Data

US 2024/0245390 A1 Jul. 25, 2024

Related U.S. Application Data

(60) Provisional application No. 63/187,990, filed on May 13, 2021.

(51) Int. Cl.

| | |
|---|---|
| ***A61B 8/08*** | (2006.01) |
| ***A61B 8/00*** | (2006.01) |
| ***A61B 8/12*** | (2006.01) |

(52) U.S. Cl.
CPC .............. *A61B 8/5207* (2013.01); *A61B 8/12* (2013.01); *A61B 8/463* (2013.01)

(58) Field of Classification Search
CPC .......... A61B 8/5207; A61B 8/12; A61B 8/463
See application file for complete search history.

(56) References Cited

U.S. PATENT DOCUMENTS 6,776,763 B2 8/2004 Nix
7,226,417 B1 6/2007 Eberle
(Continued)

FOREIGN PATENT DOCUMENTS

JP 2015527901 A * 9/2015
WO WO 2020148162 * 7/2020
(Continued)

OTHER PUBLICATIONS

JP-2015527901 machine translation (Year: 2015).*
International Search Report and Written Opinion of PCT/EP2022/059316, dated Jul. 19, 2022.

*Primary Examiner* — Alexei Bykhovski

(57) ABSTRACT

A co-registration system includes a processor circuit that displays a preview intravascular image along a longitudinal view of a blood vessel. The processor circuit receives, from an x-ray imaging device, x-ray images of the blood vessel while an intravascular catheter/guidewire moves through the blood vessel. The processor circuit receives, from the catheter, intravascular data representative of the blood vessel while the catheter moves through the blood vessel. The longitudinal view of the blood vessel is generated based on the intravascular data. The processor circuit co-registers the intravascular data to an x-ray image received from the x-ray imaging device. The processor circuit generates and displays a preview intravascular image in conjunction with the lon- (Continued)

gitudinal view and overlaid over another intravascular image or an x-ray image in response to a user input.

19 Claims, 12 Drawing Sheets

(56) References Cited

U.S. PATENT DOCUMENTS

| | | | | |
|---|---|---|---|---|
| 7,846,101 | B2 | 12/2010 | Eberle | |
| 7,930,014 | B2 | 4/2011 | Huennekens | |
| 8,290,228 | B2 | 10/2012 | Cohen | |
| 8,463,007 | B2 | 6/2013 | Steinberg | |
| 8,670,603 | B2 | 3/2014 | Tolkowsky | |
| 8,693,756 | B2 | 4/2014 | Tolkowsky | |
| 8,781,193 | B2 | 7/2014 | Steinberg | |
| 8,855,744 | B2 | 10/2014 | Tolkowsky | |
| 10,076,301 | B2 | 9/2018 | Millett | |
| 10,092,213 | B2 * | 10/2018 | Gossler | G16H 30/20 |
| 2012/0130242 | A1 * | 5/2012 | Burgess | A61B 8/12 600/443 |
| 2014/0270436 | A1 * | 9/2014 | Dascal | A61B 5/0073 382/130 |
| 2015/0305710 | A1 | 10/2015 | Stigall | |
| 2018/0052589 | A1 * | 2/2018 | Forman | G06F 3/04842 |
| 2019/0282182 | A1 | 9/2019 | Scott | |
| 2019/0282199 | A1 | 9/2019 | Merritt | |
| 2019/0282211 | A1 | 9/2019 | Merritt | |
| 2020/0029861 | A1 | 1/2020 | Rajguru | |
| 2020/0029932 | A1 | 1/2020 | Cohen | |
| 2020/0069264 | A1 | 3/2020 | Merritt | |
| 2020/0129142 | A1 | 4/2020 | Chao | |
| 2020/0129143 | A1 | 4/2020 | Di Tullio | |
| 2020/0129144 | A1 | 4/2020 | Rajguru | |
| 2020/0129147 | A1 | 4/2020 | Nair | |
| 2020/0129148 | A1 | 4/2020 | Jenkins | |
| 2020/0129158 | A1 | 4/2020 | Chao | |
| 2020/0129159 | A1 | 4/2020 | Rajguru | |
| 2020/0205671 | A1 * | 7/2020 | Tashiro | A61B 8/463 |
| 2020/0341629 | A1 * | 10/2020 | Lee | G06F 3/03547 |
| 2023/0121329 | A1 * | 4/2023 | Park | A61B 8/5223 600/437 |

FOREIGN PATENT DOCUMENTS

| | | | |
|---|---|---|---|
| WO | 2022161790 | A1 | 8/2022 |
| WO | 2022238092 | A1 | 11/2022 |
| WO | 2022238229 | A1 | 11/2022 |
| WO | 2022238276 | A1 | 11/2022 |
| WO | 2022238392 | A1 | 11/2022 |

* cited by examiner 711
740
741
790
764
741
740
760
762
763
710
720
761
730
790

PREVIEW OF INTRALUMINAL ULTRASOUND IMAGE ALONG LONGITUDINAL VIEW OF BODY LUMEN

TECHNICAL FIELD

The present disclosure relates generally to generating and displaying multiple intraluminal data (e.g. intravascular ultrasound images) simultaneously. In particular, an intravascular ultrasound (IVUS) image is displayed with a longitudinal view of the blood vessel while temporarily displaying another IVUS image acquired in the same imaging procedure.

BACKGROUND

Physicians use many different medical diagnostic systems and tools to monitor a patient's health and diagnose and treat medical conditions. Different modalities of medical diagnostic systems may provide a physician with different data relating to internal structures within a patient. These modalities include invasive devices and systems, such as intravascular systems, and non-invasive devices and systems, such as external ultrasound systems or x-ray systems. Using multiple diagnostic systems to examine a patient's anatomy provides a physician with added insight into the condition of the patient.

In the field of intravascular imaging and physiology measurement, co-registration of data from invasive devices (e.g. intravascular ultrasound (IVUS) devices) with images collected non-invasively (e.g. via x-ray angiography and/or x-ray venography) is a powerful technique for improving the efficiency and accuracy of vascular catheterization procedures. Co-registration identifies the locations of intravascular data measurements along a blood vessel by mapping the data to an x-ray image of the vessel. A physician may then see on an angiography image exactly where along the vessel a measurement was made, rather than estimate the location.

While reviewing IVUS images, either in a point-of-care setting or afterward, a physician may identify regions of concern within the vessel. These regions of concern are often areas in the vessel where constrictions limit optimal blood flow. To identify regions of concern, the physician may compare IVUS images or measurements from multiple locations along the vessel. Navigating through a large number of IVUS images and measurements may be time consuming. It is also difficult to quickly navigate from one image to another for quick comparison.

SUMMARY

Embodiments of the present disclosure are systems, devices, and methods for displaying intravascular data while temporarily displaying other data from the same data set along an image longitudinal display (ILD). For example, the intravascular data can be intravascular ultrasound (IVUS) images. An IVUS image is displayed along with an x-ray image and an ILD. Indicators on the x-ray image and/or ILD show a user where along the vessel or ILD the displayed IVUS image was acquired. As the user moves either of these indicators to different locations, different IVUS images associated with those new locations are shown.

In one aspect, while one IVUS image and its corresponding indicators are displayed on the x-ray image and/or ILD, a user may direct the system to display an additional IVUS image as a preview. For example, the user selects a different location along the ILD and the system displays a smaller window showing the preview IVUS image associated with the different location. This smaller window may be overlaid over other elements of the display. As the user moves along the ILD to other different locations, the preview IVUS image may be continuously updated to show the IVUS image associated with each location. Each displayed preview IVUS image can also include measurements relating to each image, such as a cross-sectional area of the lumen, diameter of the lumen, etc. At the direction of the user, the system may remove the smaller window with the preview IVUS images and again display the originally selected IVUS image in conjunction with its locations shown on the x-ray image and ILD. This system advantageously allows a user to quickly browse through IVUS images to identify noteworthy images and quickly compare IVUS images with the IVUS image that is currently displayed. As a result, the user may more quickly and accurately identify regions of interest along a vessel and improve the effectiveness of imaging and treatment procedures.

In an exemplary aspect, a system provided. The system comprises a processor circuit configured for communication with an intraluminal imaging catheter or guidewire, wherein the processor circuit is configured to receive a plurality of intraluminal images obtained by the intraluminal imaging catheter or guidewire during movement of the intraluminal imaging catheter or guidewire within a body lumen of a patient; output a screen display to a display in communication with the processor circuit, wherein the screen display comprises: a longitudinal view of the body lumen based on the plurality of intraluminal images; a first intraluminal image of the plurality of intraluminal images; and a first marker within the longitudinal view at a first site of the first intraluminal image; receive a user input along the longitudinal view at a second site of a second intraluminal image; and in response to the user input, modify the screen display to simultaneously display the second intraluminal image and the first intraluminal image while the first marker remains at the first site within the longitudinal view.

In one aspect, the longitudinal view of the body lumen comprises a stack of the plurality of intraluminal images. In one aspect, the user input comprises positioning a selection tool at the second site without actuation of the selection tool. In one aspect, the processor circuit is configured to receive an actuation of the selection tool; in response to the actuation, modify the screen display to replace the first intraluminal image with the second intraluminal image; and move the first marker to the second site within the longitudinal view. In one aspect, to receive the user input, the processor circuit is configured to compare the positioning of the selection tool at the second site to a threshold positioning; and detect the user input based on the comparison. In one aspect, to receive the user input, the processor circuit is configured to compare a duration of the positioning of the selection tool at the second site to a threshold duration; and detect the user input based on the comparison. In one aspect, in response to the user input, the processor circuit is configured to modify the screen display to include a second marker within the longitudinal view at the second site. In one aspect, a size of the second intraluminal image is smaller than the size of the first intraluminal image. In one aspect, the processor circuit is configured to determine the location of the second intraluminal image within the screen display based on the user input. In one aspect, the second intraluminal image is proximate to the second site within the screen display. In one aspect, the second intraluminal image is overlaid on at least a portion of the first intraluminal image. In one aspect, the screen display comprises an extraluminal image, wherein the second intraluminal image is overlaid on at least a portion of the extraluminal image. In one aspect, the processor circuit is configured for communication with an extraluminal imaging device, wherein the processor circuit is configured to receive a plurality of extraluminal images obtained by the extraluminal imaging device during the movement of the intraluminal imaging catheter or guidewire, wherein the plurality of extraluminal images are obtained without a contrast agent within the body lumen, and wherein the plurality of extraluminal images show a radiopaque portion of the intraluminal imaging catheter; co-register the plurality of intraluminal images to corresponding positions along a path of the body lumen based on the plurality of extraluminal images, wherein the extraluminal image is one of the plurality of extraluminal images, and wherein the screen display comprises a third marker within the extraluminal image at a first position of the first intraluminal image, wherein the first position corresponds to the first site within the longitudinal view. In one aspect, in response to the user input, the processor circuit is configured to modify the screen display to provide a fourth marker within the extraluminal image at a second position of the second intraluminal image while the third marker remains at the first position. In one aspect, in response to the user input, the processor circuit is configured to determine a metric of the body lumen corresponding to the second intraluminal image; wherein the second intraluminal image within the screen display comprises a graphical representation of the metric. In one aspect, the processor circuit is configured to at least one of determine a cessation of the user input or receive a further user input; and in response thereto, modify the screen display to remove the second intraluminal image such that the screen display comprises the longitudinal view; the first intraluminal image; and the marker at the first site within the longitudinal view.

In an exemplary aspect, a system is provided. The system comprises an intravascular ultrasound (IVUS) imaging catheter; and a processor circuit configured for communication with the IVUS imaging catheter, wherein the processor circuit is configured to receive a plurality of IVUS images obtained by the IVUS imaging catheter or guidewire during movement of the IVUS imaging catheter within a blood vessel of a patient; output a screen display to a display in communication with the processor circuit, wherein the first screen display comprises a longitudinal view of the blood vessel comprising a stack of the plurality of IVUS images; a first IVUS image of the plurality of IVUS images; and a marker within the longitudinal view at a first site of the first IVUS image; receive a user input along the longitudinal view at a second site of a second IVUS image, wherein the user input comprises positioning of a selection tool at second site without actuation of the selection tool; and in response to the user input, modify the screen display to display the second IVUS image, wherein the second IVUS image is overlaid on the screen display proximate to the second site along the longitudinal view; and simultaneously as the first IVUS image such that the marker remains at the first site within the longitudinal view.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
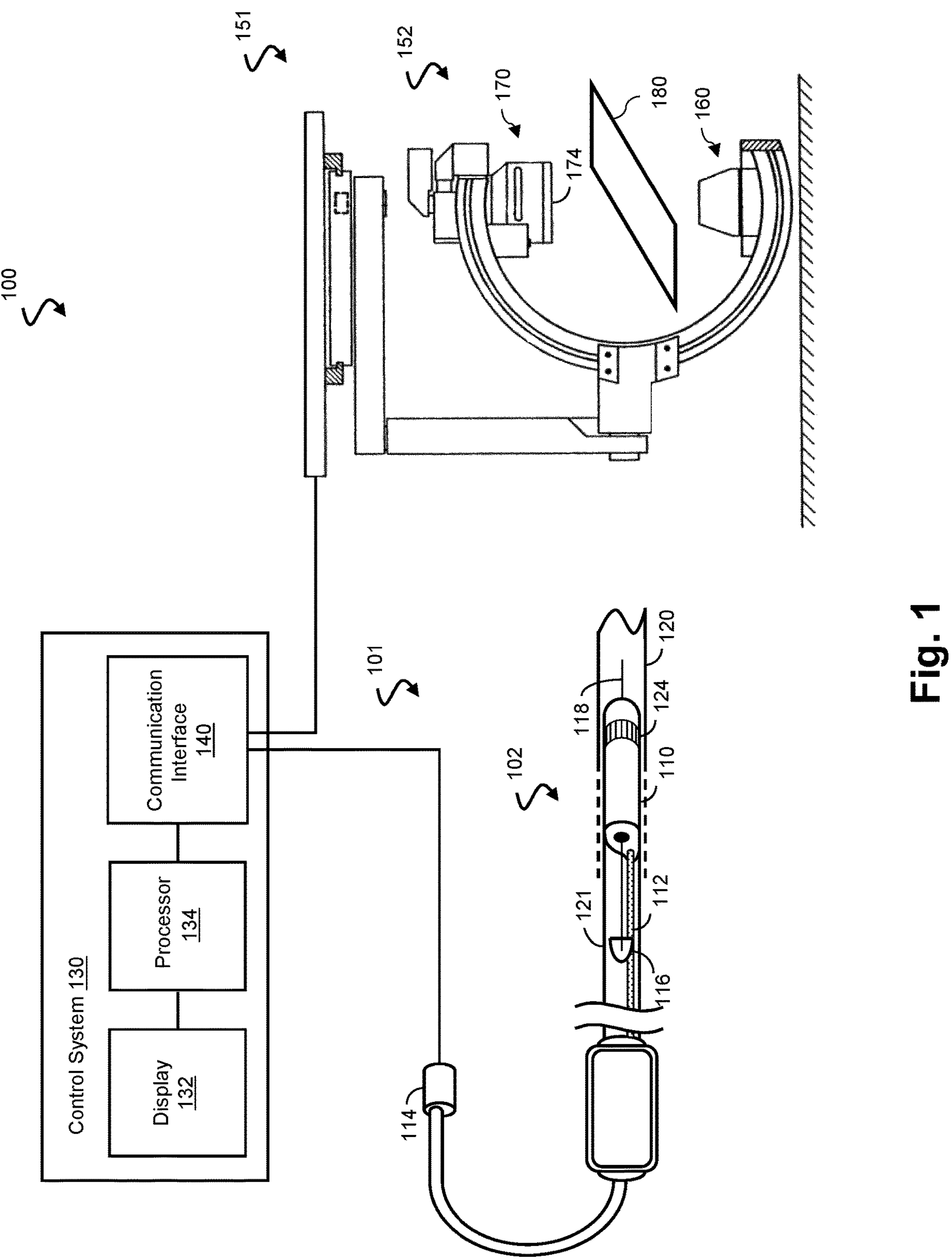
FIG. 1 is a schematic diagram of an intraluminal imaging and x-ray system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The devices, systems, and methods described herein can include one or more features described in U.S. Provisional Application No. 63/187,962, filed May 13, 2021, and titled "Coregistration Reliability with Extraluminal Image and Intraluminal Data", U.S. Provisional Application No. 63/187,964, filed May 13, 2021, and titled "Pathway Modification for Coregistration of Extraluminal Image and Intraluminal Data", U.S. Provisional Application No. 63/187,983, filed May 13, 2021, and titled "Coregistration of Intraluminal Data to Guidewire in Extraluminal Image Obtained Without Contrast", and U.S. Provisional Application No. 63/187,961, filed May 13, 2021, and titled "Intraluminal Treatment Guidance from Prior Extraluminal Imaging, Intraluminal Data, and Coregistration", each of which is incorporated by reference herein in its entirety.

The devices, systems, and methods described herein can also include one or more features described in European Application No. 21154591.8, filed Feb. 1, 2021, and titled "X-Ray and Intravascular Ultrasound Image Registration", which is incorporated by reference herein in its entirety.

The devices, systems, and methods described herein can also include one or more features described in U.S. Publication No. 2020/0129144, titled "Disease Specific and Treatment Type Specific Control of Intraluminal Ultrasound Imaging", U.S. Publication No. 2020/0129142, titled "Intraluminal Ultrasound Navigation Guidance and Associated Devices, Systems, And Methods", U.S. Publication No. 2020/0129148, titled "Intraluminal Ultrasound Imaging with Automatic and Assisted Labels And Bookmarks", U.S. Publication No. 2020/0129158, titled "Graphical Longitudinal Display for Intraluminal Ultrasound Imaging and Associated Devices, Systems, and Methods", U.S. Publication No. 2020/0129147, titled "Intraluminal Ultrasound Vessel Border Selection and Associated Devices, Systems, and Methods", U.S. Publication No. 2020/0129159, titled "Intraluminal Ultrasound Directional Guidance and Associated Devices, Systems, and Methods", U.S. Publication No. 2020/0129143, titled "Speed Determination for Intraluminal Ultrasound Imaging and Associated Devices, Systems, And Methods", each of which is incorporated by reference herein in its entirety.

FIG. 1 is a schematic diagram of an intraluminal imaging and x-ray system 100, according to aspects of the present disclosure. In some embodiments, the intraluminal imaging and x-ray system 100 may include two separate systems or be a combination of two systems: an intraluminal sensing system 101 and an extraluminal imaging system 151. The intraluminal sensing system 101 obtains medical data about a patient's body while the intraluminal device 102 is positioned inside the patient's body. For example, the intraluminal sensing system 101 can control the intraluminal device 102 to obtain intraluminal images of the inside of the patient's body while the intraluminal device 102 is inside the patient's body. The extraluminal imaging system 151 obtains medical data about the patient's body while the extraluminal imaging device 152 is positioned outside the patient's body. For example, the extraluminal imaging system 151 can control extraluminal imaging device 152 to obtain extraluminal images of the inside of the patient's body while the extraluminal imaging device 152 is outside the patient's body.

The intraluminal imaging system 101 may be in communication with the extraluminal imaging system 151 through any suitable components. Such communication may be established through a wired cable, through a wireless signal, or by any other means. In addition, the intraluminal imaging system 101 may be in continuous communication with the x-ray system 151 or may be in intermittent communication. For example, the two systems may be brought into temporary communication via a wired cable, or brought into communication via a wireless communication, or through any other suitable means at some point before, after, or during an examination. In addition, the intraluminal system 101 may receive data such as x-ray images, annotated x-ray images, metrics calculated with the x-ray imaging system 151, information regarding dates and times of examinations, types and/or severity of patient conditions or diagnoses, patient history or other patient information, or any suitable data or information from the x-ray imaging system 151. The x-ray imaging system 151 may also receive any of these data from the intraluminal imaging system 101. In some embodiments, and as shown in FIG. 1, the intraluminal imaging system 101 and the x-ray imaging system 151 may be in communication with the same control system 130. In this embodiment, both systems may be in communication with the same display 132, processor 134, and communication interface 140 shown as well as in communication with any other components implemented within the control system 130.

In some embodiments, the system 100 may not include a control system 130 in communication with the intraluminal imaging system 101 and the x-ray imaging system 151. Instead, the system 100 may include two separate control systems. For example, one control system may be in communication with or be a part of the intraluminal imaging system 101 and an additional separate control system may be in communication with or be a part of the x-ray imaging system 151. In this embodiment, the separate control systems of both the intraluminal imaging system 101 and the x-ray imaging system 151 may be similar to the control system 130. For example, each control system may include various components or systems such as a communication interface, processor, and/or a display. In this embodiment, the control system of the intraluminal imaging system 101 may perform any or all of the coregistration steps described in the present disclosure. Alternatively, the control system of the x-ray imaging system 151 may perform the coregistration steps described.

The intraluminal imaging system 101 can be an ultrasound imaging system. In some instances, the intraluminal imaging system 101 can be an intravascular ultrasound (IVUS) imaging system. The intraluminal imaging system 101 may include an intraluminal imaging device 102, such as a catheter, guide wire, or guide catheter, in communication with the control system 130. The control system 130 may include a display 132, a processor 134, and a communication interface 140 among other components. The intraluminal imaging device 102 can be an ultrasound imaging device. In some instances, the device 102 can be an IVUS imaging device, such as a solid-state IVUS device.

At a high level, the IVUS device 102 emits ultrasonic energy from a transducer array 124 included in a scanner assembly, also referred to as an IVUS imaging assembly, mounted near a distal end of the catheter device. The ultrasonic energy is reflected by tissue structures in the surrounding medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The communication interface 140 transfers the received echo signals to the processor 134 of the control system 130 where the ultrasound image (including flow information in some embodiments) is reconstructed and displayed on the display 132. The control system 130, including the processor 134, can be operable to facilitate the features of the IVUS imaging system 101 described herein. For example, the processor 134 can execute computer readable instructions stored on the non-transitory tangible computer readable medium.

The communication interface 140 facilitates communication of signals between the control system 130 and the scanner assembly 110 included in the IVUS device 102. This communication includes the steps of (1) providing commands to integrated circuit controller chip(s) included in the scanner assembly 110 to select the particular transducer array element(s), or acoustic element(s), to be used for transmit and receive, (2) providing the transmit trigger signals to the integrated circuit controller chip(s) included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) of the scanner assembly 110. In some embodiments, the communication interface 140 performs preliminary processing of the echo data prior to relaying the data to the processor 134. In examples of such embodiments, the communication interface 140 performs amplification, filtering, and/or aggregating of the data. In an embodiment, the communication interface 140 also supplies high- and low-voltage DC power to support operation of the device 102 including circuitry within the scanner assembly 110.

The processor 134 receives the echo data from the scanner assembly 110 by way of the communication interface 140 and processes the data to reconstruct an image of the tissue structures in the medium surrounding the scanner assembly 110. The processor 134 outputs image data such that an image of the lumen 120, such as a cross-sectional image of the vessel 120, is displayed on the display 132. The lumen 120 may represent fluid filled or surrounded structures, both natural and man-made. The lumen 120 may be within a body of a patient. The lumen 120 may be a blood vessel, such as an artery or a vein of a patient's vascular system, including cardiac vasculature, peripheral vasculature, neural vasculature, renal vasculature, and/or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

In some embodiments, the IVUS device includes some features similar to traditional solid-state IVUS catheters, such as the EagleEye® catheter, Visions PV 0.014P RX catheter, Visions PV 0.018 catheter, Visions PV 0.035, and Pioneer Plus catheter, each of which are available from Koninklijke Philips N.V, and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a patient interface module (PIM) connector 114 at a proximal end of the device 102. The PIM connector 114 electrically couples the transmission line bundle 112 to the communication interface 140 and physically couples the IVUS device 102 to the communication interface 140. In some embodiments, the communication interface 140 may be a PIM. In an embodiment, the IVUS device 102 further includes a guide wire exit port 116. Accordingly, in some instances the IVUS device 102 is a rapid-exchange catheter. The guide wire exit port 116 allows a guide wire 118 to be inserted towards the distal end to direct the device 102 through the vessel 120. In some embodiments, the intraluminal imaging device 102 may acquire intravascular images of any suitable imaging modality, including optical coherence tomography (OCT) and intravascular photoacoustic (IVPA).

In some embodiments, the intraluminal device 102 is a pressure sensing device (e.g., pressure-sensing guidewire) that obtains intraluminal (e.g., intravascular) pressure data, and the intraluminal system 101 is an intravascular pressure sensing system that determines pressure ratios based on the pressure data, such as fractional flow reserve (FFR), instantaneous wave-free ratio (iFR), and/or other suitable ratio between distal pressure and proximal/aortic pressure (Pd/Pa). In some embodiments, the intraluminal device 102 is a flow sensing device (e.g., flow-sensing guidewire) that obtains intraluminal (e.g., intravascular) flow data, and the intraluminal system 101 is an intravascular flow sensing system that determines flow-related values based on the pressure data, such as coronary flow reserve (CFR), flow velocity, flow volume, etc.

The x-ray imaging system 151 may include an x-ray imaging apparatus or device 152 configured to perform x-ray imaging, angiography, fluoroscopy, radiography, venography, among other imaging techniques. The x-ray imaging system 151 can generate a single x-ray image (e.g., an angiogram or venogram) or multiple (e.g., two or more) x-ray images (e.g., a video and/or fluoroscopic image stream) based on x-ray image data collected by the x-ray device 152. The x-ray imaging device 152 may be of any suitable type, for example, it may be a stationary x-ray system such as a fixed c-arm x-ray device, a mobile c-arm x-ray device, a straight arm x-ray device, or a u-arm device. The x-ray imaging device 152 may additionally be any suitable mobile device. The x-ray imaging device 152 may also be in communication with the control system 130. In some embodiments, the x-ray system 151 may include a digital radiography device or any other suitable device.

The x-ray device 152 as shown in FIG. 1 includes an x-ray source 160 and an x-ray detector 170 including an input screen 174. The x-ray source 160 and the detector 170 may be mounted at a mutual distance. Positioned between the x-ray source 160 and the x-ray detector 170 may be an anatomy of a patient or object 180. For example, the anatomy of the patient (including the vessel 120) can be positioned between the x-ray source 160 and the x-ray detector 170.

The x-ray source 160 may include an x-ray tube adapted to generate x-rays. Some aspects of the x-ray source 160 may include one or more vacuum tubes including a cathode in connection with a negative lead of a high-voltage power source and an anode in connection with a positive lead of the same power source. The cathode of the x-ray source 160 may additionally include a filament. The filament may be of any suitable type or constructed of any suitable material, including tungsten or rhenium tungsten, and may be positioned within a recessed region of the cathode. One function of the cathode may be to expel electrons from the high voltage power source and focus them into a well-defined beam aimed at the anode. The anode may also be constructed of any suitable material and may be configured to create x-radiation from the emitted electrons of the cathode. In addition, the anode may dissipate heat created in the process of generating x-radiation. The anode may be shaped as a beveled disk and, in some embodiments, may be rotated via an electric motor. The cathode and anode of the x-ray source 160 may be housed in an airtight enclosure, sometimes referred to as an envelope.

In some embodiments, the x-ray source 160 may include a radiation object focus which influences the visibility of an image. The radiation object focus may be selected by a user of the system 100 or by a manufacture of the system 100 based on characteristics such as blurring, visibility, heat-dissipating capacity, or other characteristics. In some embodiments, an operator or user of the system 100 may switch between different provided radiation object foci in a point-of-care setting.

The detector 170 may be configured to acquire x-ray images and may include the input screen 174. The input screen 174 may include one or more intensifying screens configured to absorb x-ray energy and convert the energy to light. The light may in turn expose a film. The input screen 174 may be used to convert x-ray energy to light in embodiments in which the film may be more sensitive to light than x-radiation. Different types of intensifying screens within the image intensifier may be selected depending on the region of a patient to be imaged, requirements for image detail and/or patient exposure, or any other factors. Intensifying screens may be constructed of any suitable materials, including barium lead sulfate, barium strontium sulfate, barium fluorochloride, yttrium oxysulfide, or any other suitable material. The input screen 374 may be a fluorescent screen or a film positioned directly adjacent to a fluorescent screen. In some embodiments, the input screen 374 may also include a protective screen to shield circuitry or components within the detector 370 from the surrounding environment. In some embodiments, the x-ray detector 170 may include a flat panel detector (FPD). The detector 170 may be an indirect conversion FPD or a direct conversion FPD. The detector 170 may also include charge-coupled devices (CCDs). The x-ray detector 370 may additionally be referred to as an x-ray sensor.

The object 180 may be any suitable object to be imaged. In an exemplary embodiment, the object may be the anatomy of a patient. More specifically, the anatomy to be imaged may include chest, abdomen, the pelvic region, neck, legs, head, feet, a region with cardiac vasculature, or a region containing the peripheral vasculature of a patient and may include various anatomical structures such as, but not limited to, organs, tissue, blood vessels and blood, gases, or any other anatomical structures or objects. In other embodiments, the object may be or include man-made structures.

In some embodiments, the x-ray imaging system 151 may be configured to obtain x-ray images without contrast. In some embodiments, the x-ray imaging system 151 may be configured to obtain x-ray images with contrast (e.g., angiogram or venogram). In such embodiments, a contrast agent or x-ray dye may be introduced to a patient's anatomy before imaging. The contrast agent may also be referred to as a radiocontrast agent, contrast material, contrast dye, or contrast media. The contrast dye may be of any suitable material, chemical, or compound and may be a liquid, powder, paste, tablet, or of any other suitable form. For example, the contrast dye may be iodine-based compounds, barium sulfate compounds, gadolinium-based compounds, or any other suitable compounds. The contrast agent may be used to enhance the visibility of internal fluids or structures within a patient's anatomy. The contrast agent may absorb external x-rays, resulting in decreased exposure on the x-ray detector 170.

In some embodiments, the extraluminal imaging system 151 could be any suitable extraluminal imaging device, such as computed tomography (CT) or magnetic resonance imaging (MRI).

When the control system 130 is in communication with the x-ray system 151, the communication interface 140 facilitates communication of signals between the control system 130 and the x-ray device 152. This communication includes providing control commands to the x-ray source 160 and/or the x-ray detector 170 of the x-ray device 152 and receiving data from the x-ray device 152. In some embodiments, the communication interface 140 performs preliminary processing of the x-ray data prior to relaying the data to the processor 134. In examples of such embodiments, the communication interface 140 may perform amplification, filtering, and/or aggregating of the data. In an embodiment, the communication interface 140 also supplies high- and low-voltage DC power to support operation of the device 152 including circuitry within the device.

The processor 134 receives the x-ray data from the x-ray device 152 by way of the communication interface 140 and processes the data to reconstruct an image of the anatomy being imaged. The processor 134 outputs image data such that an image is displayed on the display 132. In an embodiment in which the contrast agent is introduced to the anatomy of a patient and a venogram is to be generated, the particular areas of interest to be imaged may be one or more blood vessels or other section or part of the human vasculature. The contrast agent may identify fluid filled structures, both natural and/or man-made, such as arteries or veins of a patient's vascular system, including cardiac vasculature, peripheral vasculature, neural vasculature, renal vasculature, and/or any other suitable lumen inside the body. For example, the x-ray device 152 may be used to examine any number of anatomical locations and tissue types, including without limitation all the organs, fluids, or other structures or parts of an anatomy previously mentioned. In addition to natural structures, the x-ray device 152 may be used to examine man-made structures such as any of the previously mentioned structures.

The processor 134 may be configured to receive an x-ray image that was stored by the x-ray imaging device 152 during a clinical procedure. The images may be further enhanced by other information such as patient history, patient record, IVUS imaging, pre-operative ultrasound imaging, pre-operative CT, or any other suitable data.

Figure 2:
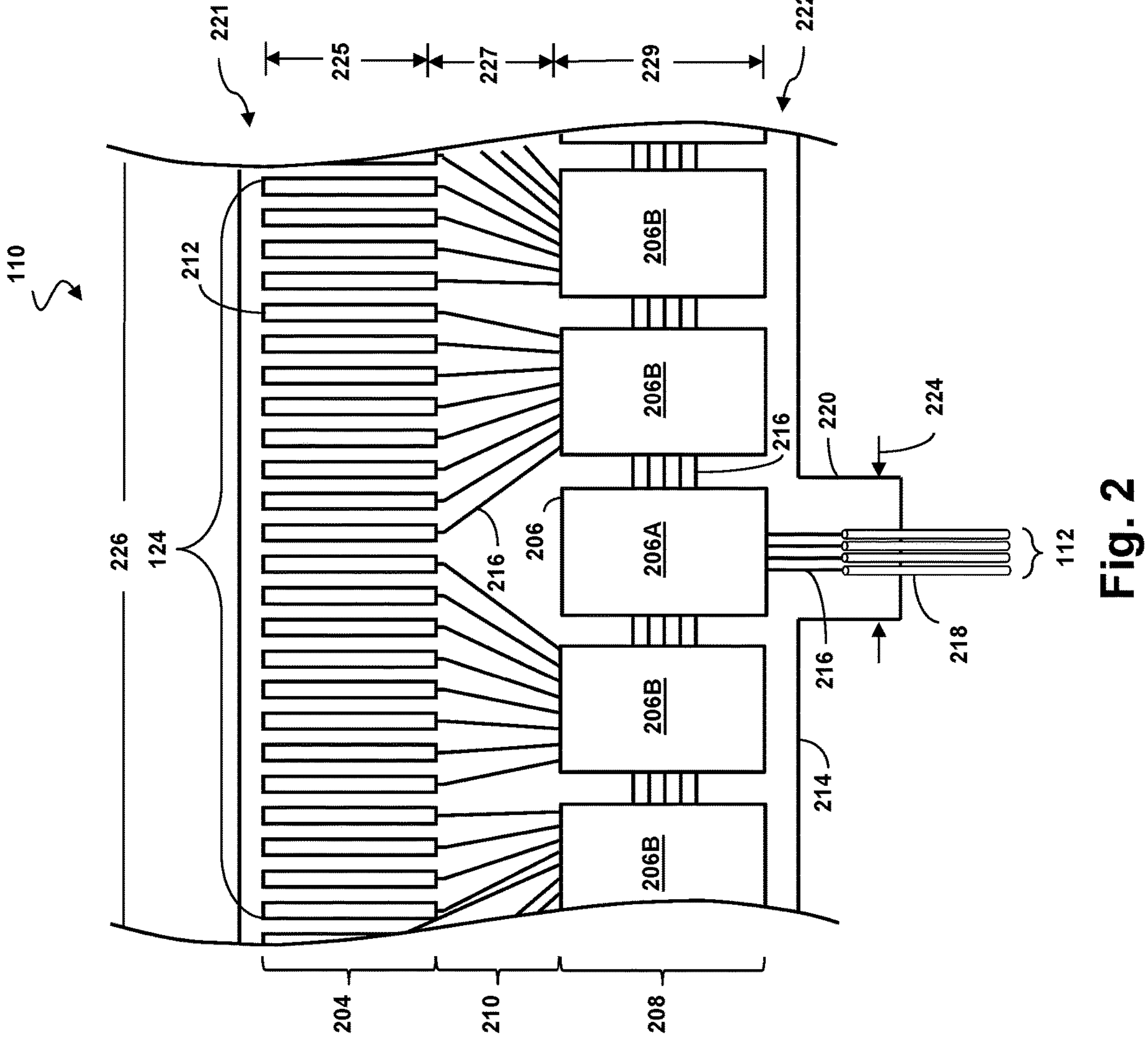
FIG. 2 is a diagrammatic top view of an ultrasound imaging assembly in a flat configuration, according to aspects of the present disclosure.

FIG. 2 is a diagrammatic top view of a portion of a flexible assembly 110, according to aspects of the present disclosure. The flexible assembly 110 includes a transducer array 124 formed in a transducer region 204 and transducer control logic dies 206 (including dies 206A and 206B) formed in a control region 208, with a transition region 210 disposed therebetween. The transducer array 124 includes an array of ultrasound transducer elements 212. The transducer control logic dies 206 are mounted on a flexible substrate 214 into which the transducer elements 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducer elements 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 m and 100 m, with some particular embodiments being between 5 m and 25.1 m, e.g., 6 m.

The set of transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 112, between a processing system, e.g., processing system 106, and the flexible assembly 110. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a plurality of transducer elements 512 positioned on a transducer element 212 to emit an ultrasonic signal and selects a transducer element 212 to receive an echo. In the depicted embodiment, the master controller 206A does not directly control any transducer elements 212. In other embodiments, the master controller 206A drives the same number of transducer elements 212 as the slave controllers 206B or drives a reduced set of transducer elements 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducer elements 212, in an embodiment, the flexible substrate 214 includes conductive traces 216 formed in the film layer that carry signals between the control logic dies 206 and the transducer elements 212. In particular, the conductive traces 216 providing communication between the control logic dies 206 and the transducer elements 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 m. For example, in an embodiment, 5 m conductive traces 216 are separated by 5 m of space. The width of a conductive trace 216 on the flexible substrate may be further determined by the width of the conductor 218 to be coupled to the trace or pad.

The flexible substrate 214 can include a conductor interface 220 in some embodiments. The conductor interface 220 can be in a location of the flexible substrate 214 where the conductors 218 of the cable 112 are coupled to the flexible substrate 214. For example, the bare conductors of the cable 112 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
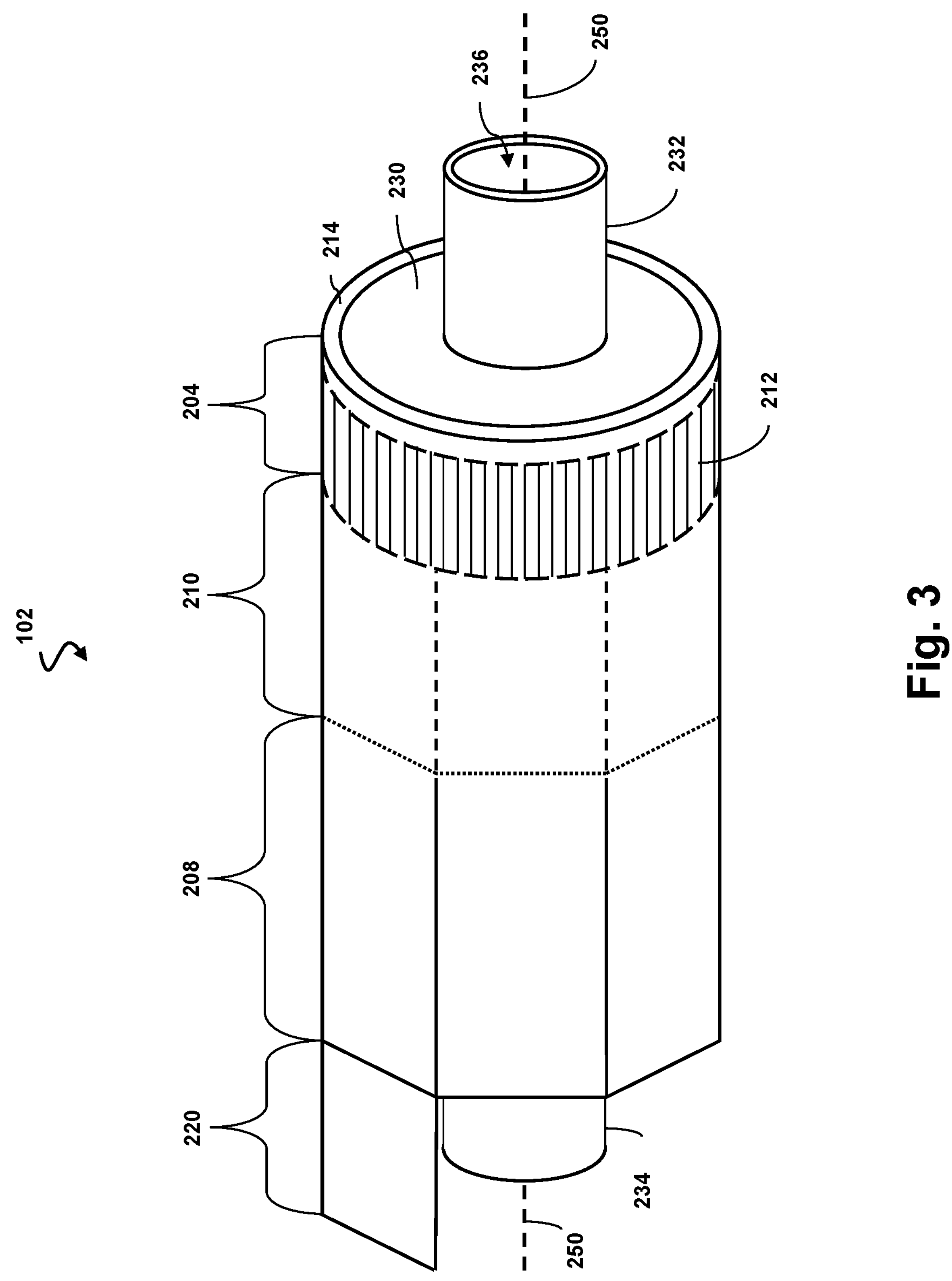
FIG. 3 is a diagrammatic perspective view of the ultrasound imaging assembly shown in FIG. 2 in a rolled configuration around a support member, according to aspects of the present disclosure.

FIG. 3 illustrates a perspective view of the scanner assembly 110 in a rolled configuration. In some instances, the flexible substrate 214 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

Depending on the application and embodiment of the presently disclosed invention, transducer elements 212 may be piezoelectric transducers, single crystal transducer, or PZT (lead zirconate titanate) transducers. In other embodiments, the transducer elements of transducer array 124 may be flexural transducers, piezoelectric micromachined ultrasonic transducers (PMUTs), capacitive micromachined ultrasonic transducers (CMUTs), or any other suitable type of transducer element. In such embodiments, transducer elements 212 may comprise an elongate semiconductor material or other suitable material that allows micromachining or similar methods of disposing extremely small elements or circuitry on a substrate.

In some embodiments, the transducer elements 212 and the controllers 206 can be positioned in an annular configuration, such as a circular configuration or in a polygon configuration, around a longitudinal axis 250 of a support member 230. It is understood that the longitudinal axis 250 of the support member 230 may also be referred to as the longitudinal axis of the scanner assembly 110, the flexible elongate member 121, or the device 102. For example, a cross-sectional profile of the imaging assembly 110 at the transducer elements 212 and/or the controllers 206 can be a circle or a polygon. Any suitable annular polygon shape can be implemented, such as one based on the number of controllers or transducers, flexibility of the controllers or transducers, etc. Some examples may include a pentagon, hexagon, heptagon, octagon, nonagon, decagon, etc. In some examples, the transducer controllers 206 may be used for controlling the ultrasound transducers 512 of transducer elements 212 to obtain imaging data associated with the vessel 120.

The support member 230 can be referenced as a unibody in some instances. The support member 230 can be composed of a metallic material, such as stainless steel, or a non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. In some embodiments, support member 230 may be composed of 303 stainless steel. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process or a micro injection molding process.

Figure 4:
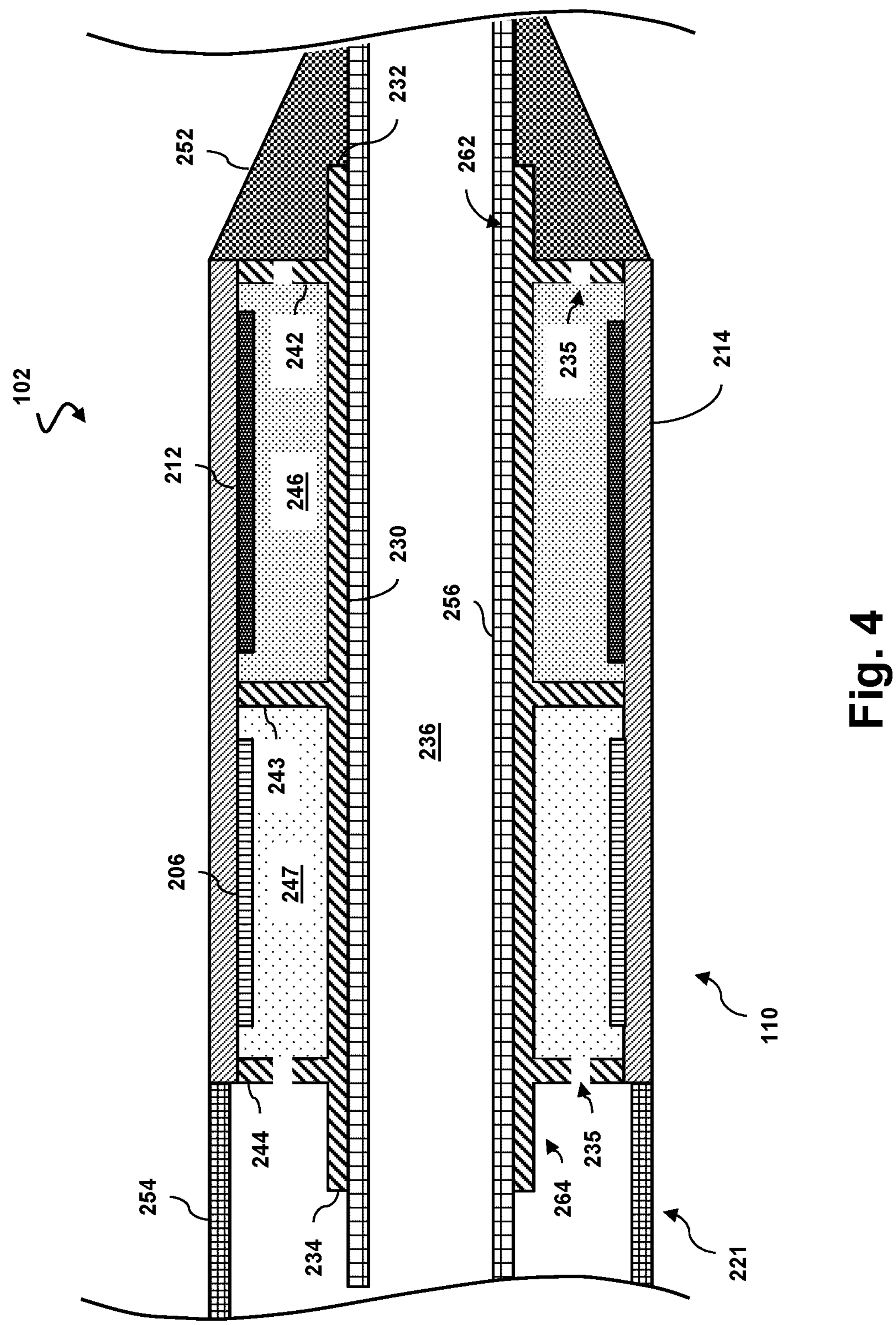
FIG. 4 is a diagrammatic cross-sectional side view of the ultrasound imaging assembly shown in FIG. 3, according to aspects of the present disclosure.

Referring now to FIG. 4, shown therein is a diagrammatic cross-sectional side view of a distal portion of the intraluminal imaging device 102, including the flexible substrate 214 and the support member 230, according to aspects of the present disclosure. The lumen 236 may be connected with the entry/exit port 116 and is sized and shaped to receive the guide wire 118 (FIG. 1). In some embodiments, the support member 230 may be integrally formed as a unitary structure, while in other embodiments the support member 230 may be formed of different components, such as a ferrule and stands 242, 243, and 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 243, and 244 that extend vertically are provided at the distal, central, and proximal portions respectively, of the support member 230. The stands 242, 243, and 244 elevate and support the distal, central, and proximal portions of the flexible substrate 214. In that regard, portions of the flexible substrate 214, such as the transducer portion 204 (or transducer region 204), can be spaced from a central body portion of the support member 230 extending between the stands 242, 243, and 244. The stands 242, 243, 244 can have the same outer diameter or different outer diameters. For example, the distal stand 242 can have a larger or smaller outer diameter than the central stand 243 and/or proximal stand 244 and can also have special features for rotational alignment as well as control chip placement and connection.

To improve acoustic performance, the cavity between the transducer array 212 and the surface of the support member 230 may be filled with an acoustic backing material 246. The liquid backing material 246 can be introduced between the flexible substrate 214 and the support member 230 via passageway 235 in the stand 242, or through additional recesses as will be discussed in more detail hereafter. The backing material 246 may serve to attenuate ultrasound energy emitted by the transducer array 212 that propagates in the undesired, inward direction.

The cavity between the circuit controller chips 206 and the surface of the support member 230 may be filled with an underfill material 247. The underfill material 247 may be an adhesive material (e.g. an epoxy) which provides structural support for the circuit controller chips 206 and/or the flexible substrate 214. The underfill 247 may additionally be any suitable material.

In some embodiments, the central body portion of the support member can include recesses allowing fluid communication between the lumen of the unibody and the cavities between the flexible substrate 214 and the support member 230. Acoustic backing material 246 and/or underfill material 247 can be introduced via the cavities (during an assembly process, prior to the inner member 256 extending through the lumen of the unibody. In some embodiments, suction can be applied via the passageways 235 of one of the stands 242, 244, or to any other suitable recess while the liquid backing material 246 is fed between the flexible substrate 214 and the support member 230 via the passageways 235 of the other of the stands 242, 244, or any other suitable recess. The backing material can be cured to allow it to solidify and set. In various embodiments, the support member 230 includes more than three stands 242, 243, and 244, only one or two of the stands 242, 243, 244, or none of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions of the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the proximal end of flexible substrate 214. A distal tip member 252 is coupled to the distal portion 262 of the support member 230. For example, the distal member 252 is positioned around the distal flange 232. The tip member 252 can abut and be in contact with the distal end of flexible substrate 214 and the stand 242. In other embodiments, the proximal end of the tip member 252 may be received within the distal end of the flexible substrate 214 in its rolled configuration. In some embodiments there may be a gap between the flexible substrate 214 and the tip member 252. The distal member 252 can be the distal-most component of the intraluminal imaging device 102. The distal tip member 252 may be a flexible, polymeric component that defines the distal-most end of the imaging device 102. The distal tip member 252 may additionally define a lumen in communication with the lumen 236 defined by support member 230. The guide wire 118 may extend through lumen 236 as well as the lumen defined by the tip member 252.

One or more adhesives can be disposed between various components at the distal portion of the intraluminal imaging device 102. For example, one or more of the flexible substrate 214, the support member 230, the distal member 252, the proximal inner member 256, the transducer array 212, and/or the proximal outer member 254 can be coupled to one another via an adhesive. Stated differently, the adhesive can be in contact with e.g. the transducer array 212, the flexible substrate 214, the support member 230, the distal member 252, the proximal inner member 256, and/or the proximal outer member 254, among other components.

Figure 5:
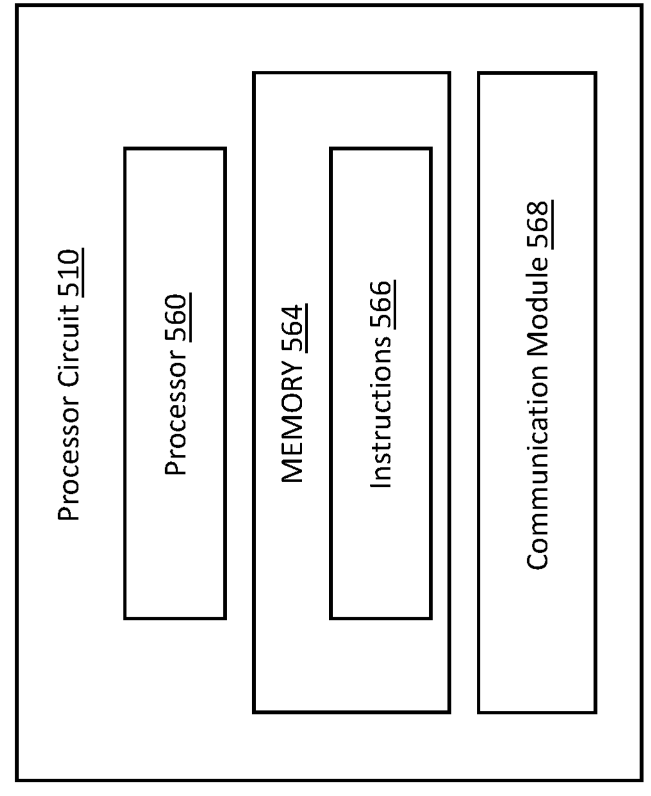
FIG. 5 is a schematic diagram of a processor circuit, according to aspects of the present disclosure.

FIG. 5 is a schematic diagram of a processor circuit, according to aspects of the present disclosure. The processor circuit 510 may be implemented in the control system 130 of FIG. 1, the intraluminal imaging system 101, and/or the x-ray imaging system 151, or any other suitable location. In an example, the processor circuit 510 may be in communication with intraluminal imaging device 102, the x-ray imaging device 152, the display 132 within the system 100. The processor circuit 510 may include the processor 134 and/or the communication interface 140 (FIG. 1). One or more processor circuits 510 are configured to execute the operations described herein. As shown, the processor circuit 510 may include a processor 560, a memory 564, and a communication module 568. These elements may be in direct or indirect communication with each other, for example via one or more buses.

The processor 560 may include a CPU, a GPU, a DSP, an application-specific integrated circuit (ASIC), a controller, an FPGA, another hardware device, a firmware device, or any combination thereof configured to perform the operations described herein. The processor 560 may also be implemented as a combination of computing devices, e.g., a combination of a DSP and a microprocessor, a plurality of microprocessors, one or more microprocessors in conjunction with a DSP core, or any other such configuration.

The memory 564 may include a cache memory (e.g., a cache memory of the processor 560), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 564 includes a non-transitory computer-readable medium. The memory 564 may store instructions 566. The instructions 566 may include instructions that, when executed by the processor 560, cause the processor 560 to perform the operations described herein with reference to the probe 110 and/or the host 130 (FIG. 1). Instructions 566 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 568 can include any electronic circuitry and/or logic circuitry to facilitate direct or indirect communication of data between the processor circuit 510, the probe 110, and/or the display 132 and/or display 132. In that regard, the communication module 568 can be an input/output (I/O) device. In some instances, the communication module 568 facilitates direct or indirect communication between various elements of the processor circuit 510 and/or the probe 110 (FIG. 1) and/or the host 130 (FIG. 1).

Figure 6:
FIG. 6 is a diagrammatic view of an x-ray fluoroscopy image illustrating a pullback procedure, according to aspects of the present disclosure.
Figure 6:
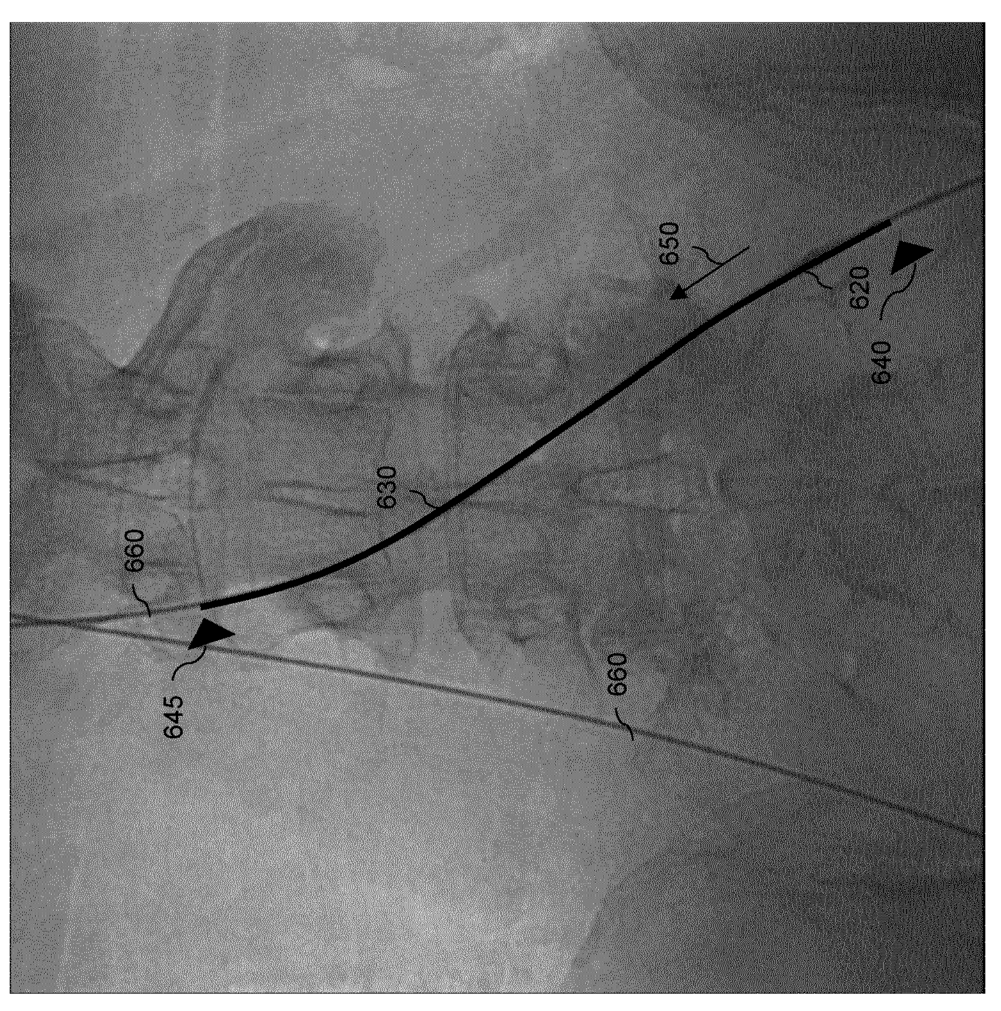

FIG. 6 is a diagrammatic view of an x-ray fluoroscopy image illustrating a pullback procedure, according to aspects of the present disclosure. FIG. 6 depicts an x-ray fluoroscopy image 610 showing an intravascular device 620 and guidewires 660. FIG. 6 additionally depicts an intravascular device path 630, a starting indicator 640, an ending indicator 645, and a directional arrow 650.

During a pullback procedure, one or more guidewires 660 may be positioned within one or more lumens of a patient. Because the guidewire 660 may be constructed of a flexible material, the shape of the guidewire 660 may conform to the shape of the lumen in which the guidewire 660 is positioned. The guidewire 660 may include a flexible elongate member. An intravascular device 620 may be positioned within the lumen and travel through the lumen along a guidewire 660, which is positioned within a guidewire lumen of the intravascular device 620. The intravascular device 620 can be a catheter or a guide catheter. The intravascular device 620 may be an IVUS catheter. The device 620 may be constructed of a flexible material, such that the shape of the device 620 may match the curvature of the lumen in which the device 620 is positioned. The intravascular device 620 may include a flexible elongate member. In the fluoroscopy image 610, a radiopaque portion of the intravascular device 620 is visible. The intravascular device 620 may be substantially similar to the device 102 of the intraluminal ultrasound imaging system 101. A user of the system 100 may position the intravascular device 620 at a starting location shown by the indicator 640. With the intravascular device 620 placed at the starting location, the user may begin acquiring fluoroscopy images with the x-ray imaging system 151. The image 610 may be one of the many x-ray fluoroscopy images obtained during the pullback. In some embodiments, the fluoroscopy image 610 is an x-ray image obtained while no contrast agent is present within the patient anatomy. In such an embodiment, the lumens (e.g., blood vessel) of the patient may be identified primarily by the positioning of the guidewires 660 within the lumens. In other embodiments, the image 610 may be an x-ray image obtained while a contrast agent is present within the patient anatomy. The contrast agent may make vessel lumens visible within the image 610.

One or a plurality of radiopaque portions of the guidewire 660 are visible in the x-ray image(s) 610 obtained without contrast. The radiopaque portions can be one length or a plurality of lengths of the guidewire 660. In some embodiments, the radiopaque portions of the guidewire 660 are one or a plurality of radiopaque markers. The radiopaque markers can be made of a different material that is more radiopaque than the material used to form other parts of the guidewire 660. In some embodiments, all or substantially all of the guidewire 660 can be radiopaque. In some embodiments, all or substantially all of the portion of the guidewire 660 within the patient body can be radiopaque. In some embodiments, all or substantially all of the distal portion of the guidewire 660 (e.g., the portion of the guidewire being imaged by x-ray) can be radiopaque. For example, the guidewire 660 can be sufficiently thick (e.g., a sufficiently large diameter) to provide radiopacity in x-ray images 610. Such embodiments can include clinical applications in the peripheral venous system, which can involve guidewires with a diameter between 0.014" and 0.038", including values such as 0.014", 0.018", 0.038", and/or other values both larger and smaller.

While the x-ray imaging system 151 acquires fluoroscopy images, the user of the system 100 may then begin to move device 620 through the patient lumen along the guidewire 660. The user may pull the device in a direction shown by the arrow 650. As the device 620 moves along the guidewire 660 through the lumen, the device 620 shown in newly acquired fluoroscopy images is shown to move in the direction shown by the arrow 650. The user may continue to pull the device 620 along the guidewire 660 until an ending position 645. The path taken by the device 620 during the pullback procedure may be illustrated by the path 630 within FIG. 6.

As the device 620 moves from the starting position shown by the indicator 640 to the ending position shown by the indicator 645, it may acquire any suitable intravascular data, such as IVUS images. After the device 620 has moved to the ending position, the user may stop acquiring fluoroscopy images with the x-ray imaging system 151 and may remove the device 620 from the lumen. Because the intravascular data was obtained with the device 620 while fluoroscopy images were simultaneously acquired, the intravascular data may be coregistered to the places along the path 630 at which each datum was collected and displayed in relation to that location along the path 630 and/or a representative fluoroscopy image as will be described with greater detail with reference to FIG. 7.

In some embodiments, the intravascular device 620 may be moved in an opposite direction. For example, the device may be moved from the position of indicator 645 to the position of indicator 640. In other words, the device 620 may move from a distal region to a proximal region (e.g., a pullback) or may move from a proximal region to a distal region (e.g., push forward) during the imaging procedure.

It is noted, that the starting and ending positions may represent target locations during an IVUS imaging procedure. Any indicators, such as indicators 640 and/or 645, identifying these locations may not be visible within an x-ray image displayed to a user during a pullback procedure. For example, during an imaging procedure, the system may identify the starting location of the device 620 on the display, but the ending location of the device 620 is not known because the procedure is still in the process of being completed. However, after an IVUS imaging procedure or pullback procedure is completed, during a review phase of the process, indicators 640 and/or 645 identifying both the starting location and the ending location may be displayed to a user of the system.

Figure 7:
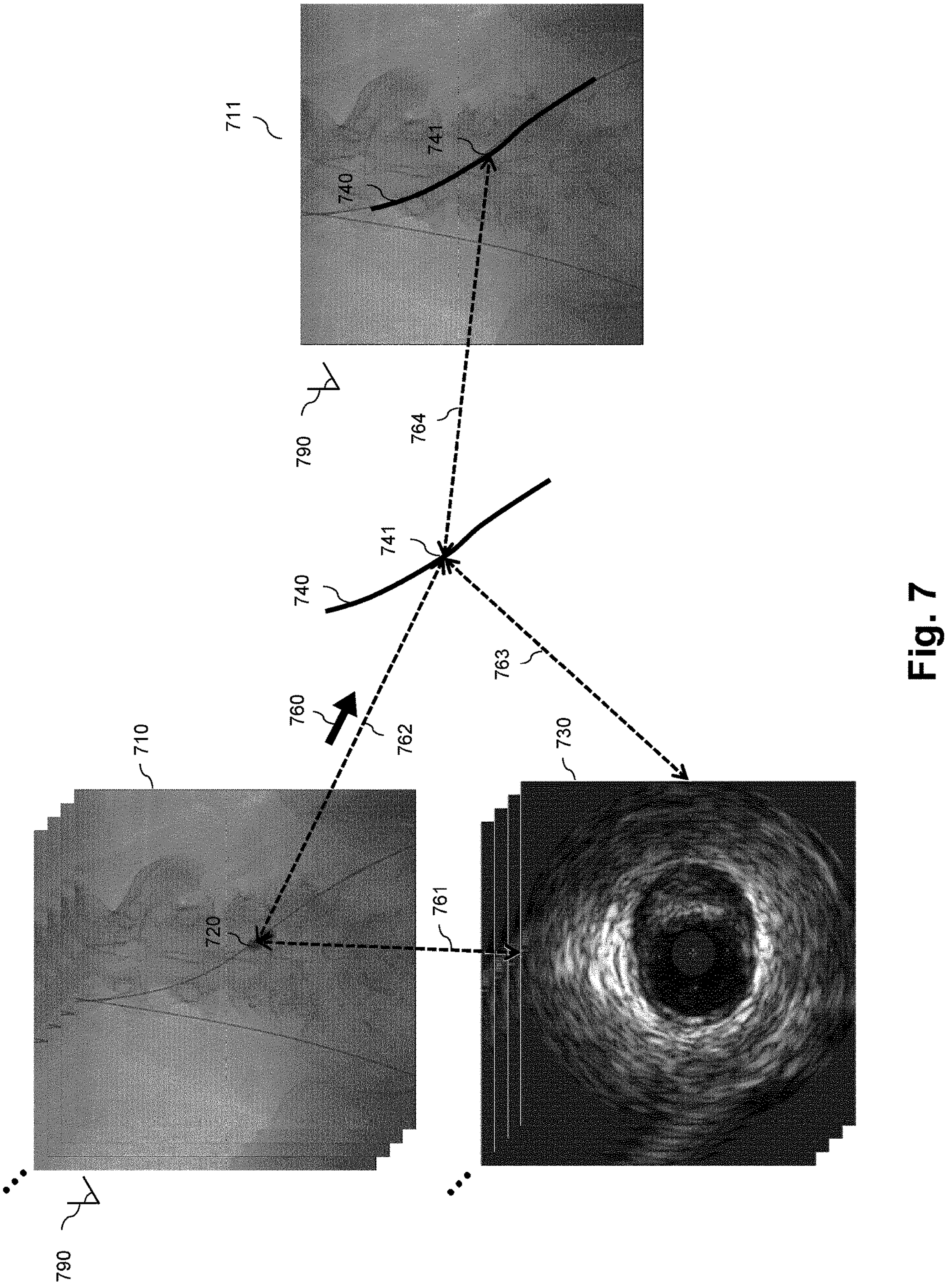
FIG. 7 is a diagrammatic view of a relationship between x-ray fluoroscopy images, intravascular data, and a path defined by the motion of an intravascular device, according to aspects of the present disclosure.

FIG. 7 is a diagrammatic view of a relationship between x-ray fluoroscopy images 710, intravascular data 730, and a path 740 defined by the motion of an intravascular device, according to aspects of the present disclosure. FIG. 7 describes a method of coregistering intravascular data 730 including intravascular images with corresponding locations on one or more fluoroscopy images 710 of the same region of a patient's anatomy.

The patient anatomy may be imaged with an x-ray device while a physician performs a pullback with an intravascular device 720, e.g., while the intravascular device 720 moves through a blood vessel of the anatomy. The intravascular device may be substantially similar to the intravascular device 102 described with reference to FIG. 1. The x-ray device used to obtain the fluoroscopy images 710 may be substantially similar to the x-ray device 152 of FIG. 1. In some embodiments, the fluoroscopy images 710 may be obtained while no contrast agent is present within the patient vasculature. Such an embodiment is shown by the fluoroscopy images 710 in FIG. 7. The radiopaque portion of the intravascular device 720 is visible within the fluoroscopy image 710. The fluoroscopy images 710 may correspond to a continuous image stream of fluoroscopy images and may be obtained as the patient anatomy is exposed to a reduced dose of x-radiation. It is noted that the fluoroscopy images 710 may be acquired with the x-ray source 160 and the x-ray detector 170 positioned at any suitable angle in relation to the patient anatomy. This angle is shown by angle 790.

The intravascular device 720 may be any suitable intravascular device. As the intravascular device 720 moves through the patient vasculature, the x-ray imaging system may acquire multiple fluoroscopy images 710 showing the radiopaque portion of the intravascular device 720. In this way, each fluoroscopy image 710 shown in FIG. 7 may depict the intravascular device 720 positioned at a different location such that a processor circuit may track the position of the intravascular device 720 over time.

As the intravascular device 720 is pulled through the patient vasculature, it may acquire intravascular data 730. In an example, the intravascular data 730 shown in FIG. 7 may be IVUS images. However, the intravascular data may be any suitable data, including IVUS images, FFR data, iFR data, OCT images, intravascular photoacoustic (IVPA) images, or any other measurements or metrics relating to blood pressure, blood flow, lumen structure, or other physiological data acquired during a pullback of an intravascular device.

As the physician pulls the intravascular device 720 through the patient vasculature, each intravascular data point 730 acquired by the intravascular device 720 may be associated with a position within the patient anatomy in the fluoroscopy images 710, as indicated by the arrow 761. For example, the first IVUS image 730 shown in FIG. 7 may be associated with the first fluoroscopy image 710. The first IVUS image 730 may be an image acquired by the intravascular device 720 at a position within the vasculature, as depicted in the first fluoroscopy image 710 as shown by the intravascular device 720 within the image 710. Similarly, an additional IVUS image 730 may be associated with an additional fluoroscopy image 710 showing the intravascular device 720 at a new location within the image 710, and so on. The processor circuit may determine the locations of the intravascular device 720 within each acquired x-ray image 710 by any suitable method. For example, the processor circuit may perform various image processing techniques, such as edge identification of the radiopaque marker, pixel-by-pixel analysis to determine transition between light pixels and dark pixels, filtering, or any other suitable techniques to determine the location of the imaging device 720. In some embodiments, the processor circuit may use various deep learning techniques such as neural networks or any other suitable techniques to identify the locations of the imaging device 720 within the x-ray images 710.

Any suitable number of IVUS images or other intravascular data points 730 may be acquired during an intravascular device pullback and any suitable number of fluoroscopy images 710 may be obtained. In some embodiments, there may be a one-to-one ratio of fluoroscopy images 710 and intravascular data 730. In other embodiments, there may be differing numbers of fluoroscopy images 710 and/or intravascular data 730. The process of co-registering the intravascular data 730 with one or more x-ray images may include some features similar to those described in U.S. Pat. No. 7,930,014, titled, "VASCULAR IMAGE CO-REGISTRATION," and filed Jan. 11, 2006, which is hereby incorporated by reference in its entirety. The co-registration process may also include some features similar to those described in U.S. Pat. Nos. 8,290,228, 8,463,007, 8,670,603, 8,693,756, 8,781,193, 8,855,744, and 10,076,301, all of which are also hereby incorporated by reference in their entirety.

The system 100 may additionally generate a fluoroscopy-based 2D pathway 740 defined by the positions of the intravascular device 720 within the x-ray fluoroscopy images 710. The different positions of the intravascular device 720 during pullback, as shown in the fluoroscopy images 710, may define a two-dimensional pathway 740, as shown by the arrow 760. The fluoroscopy-based 2D pathway 740 reflects the path of one or more radiopaque portions of the intravascular device 720 as it moved through the patient vasculature as observed from the angle 790 by the x-ray imaging device 152. The fluoroscopy-based 2D pathway 740 defines the path as measured by the x-ray device which acquired the fluoroscopy images 710, and therefore shows the path from the same angle 790 at which the fluoroscopy images were acquired. Stated differently, the 2D pathway 740 describes the projection of the 3D path followed by the device onto the imaging plane at the imaging angle 790.

As shown by the arrow 762, because the two-dimensional path 740 is generated based on the fluoroscopy images 710, each position along the two-dimensional path 740 may be associated with one or more fluoroscopy images 710. As an example, at a location 741 along the path 740, the first fluoroscopy image 710 may depict the intravascular device 720 at that same position 741. In addition, because a correspondence was also established between the fluoroscopy images 710 and the intravascular data 730 as shown by the arrow 761, intravascular data 730, such as the first IVUS image shown, may also be associated with the location 741 along the path 740 as shown by the arrow 763.

Finally, the path 740 generated based on the locations of the intravascular device 720 within the fluoroscopy images 710 may be overlaid onto any suitable fluoroscopy image 711 (e.g., one of the fluoroscopic images 710 in the fluoroscopic image stream). In this way, any location along the path 740 displayed on the fluoroscopy image 711 may be associated with IVUS data such as an IVUS image 730, as shown by the arrow 764. For example, IVUS image 730 shown in FIG. 7 may be acquired simultaneously with the fluoroscopy image 710 shown and the two may be associated with each other as shown by the arrow 761. The fluoroscopy image 710 may then indicate the location of the intravascular device 720 along the path 740, as shown by the arrow 762, thus associating the IVUS image 730 with the location 741 along the path 740 as shown by the arrow 763. Finally, the IVUS image 730 may be associated with the location within the fluoroscopy image 710 at which it was acquired by overlaying the path 740 with associated data on the fluoroscopy image 711. The pathway 740 itself may or may not be displayed on the image 711.

In the illustrated embodiment of FIG. 7, the co-registered IVUS images are associated with one of the fluoroscopic images obtained without contrast such that that the position at which the IVUS images are obtained is known relative to locations along the guidewire. In other embodiments, the co-registered IVUS images are associated with an x-ray image obtained with contrast (in which the vessel is visible) such that that the position at which the IVUS images are obtained is known relative to locations along the vessel.

Figure 8:
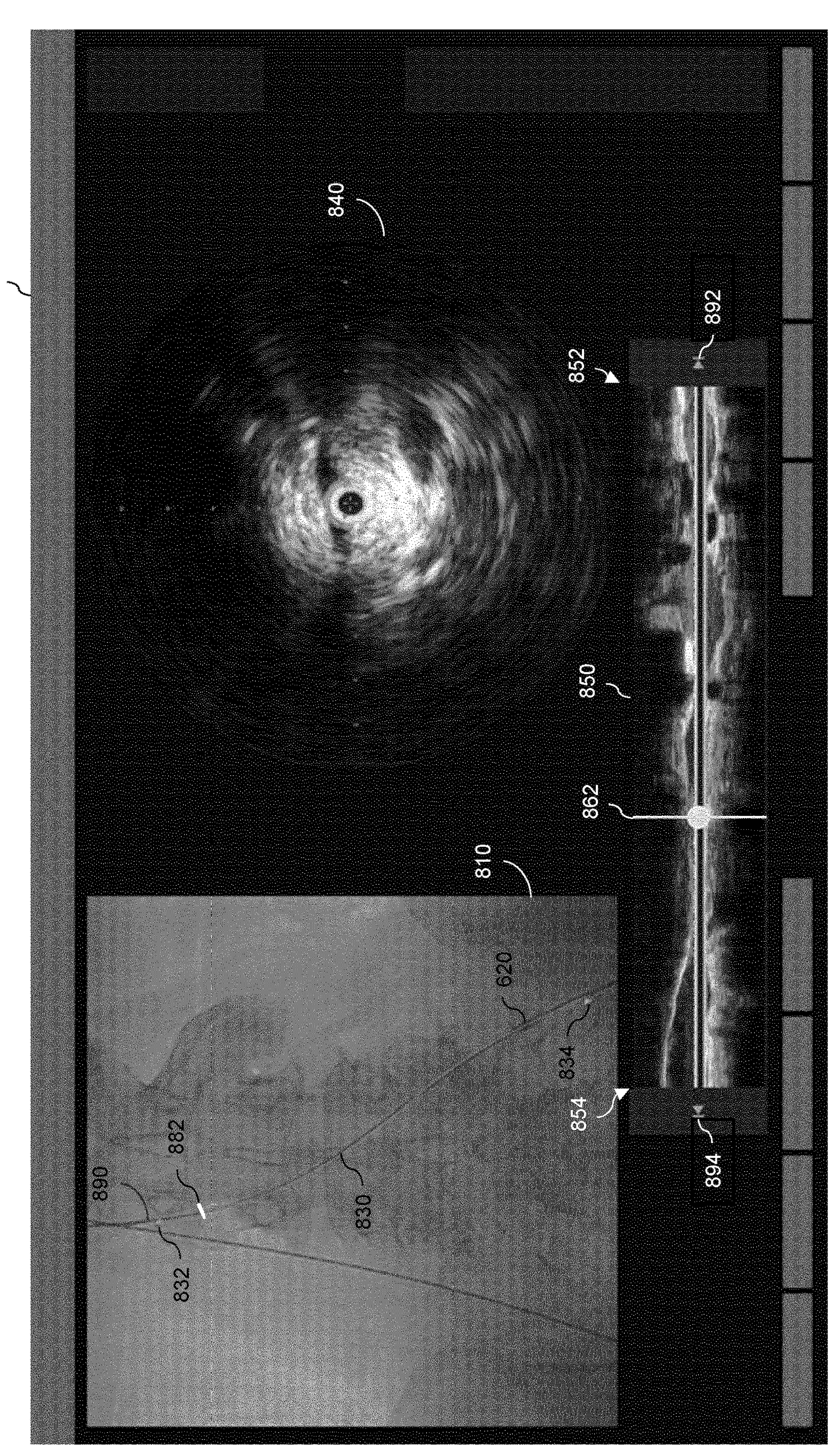
FIG. 8 is a diagrammatic view of a graphical user interface displaying an intravascular image coregistered to an x-ray image, according to aspects of the present disclosure.

FIG. 8 is a diagrammatic view of a graphical user interface 800 displaying an intravascular image 840 coregistered to an x-ray image 810, according to aspects of the present disclosure. The graphical user interface 800 may include an x-ray image 810, an IVUS image 840, and a longitudinal view 850 of the vessel. The longitudinal view 850 can be an ILD, such an in line digital or image longitudinal display.

The x-ray image 810 may be displayed to a user of the system 100 within the graphical user interface 800. However, the x-ray image 810 need not be obtained or displayed. Indeed, coregistration between any intravascular data and extraluminal data need not be performed. Rather, the elements of the present disclosure may be performed only with an IVUS image 840 and a corresponding ILD 850. In embodiments where an x-ray image 810 is obtained, the x-ray image 810 may be acquired with the x-ray imaging system 151 and may be received by the processor 134 of the system 100 (FIG. 1). The x-ray image 800 may be an x-ray image acquired during an imaging procedure in which no contrast agent is added to the patient vasculature. The image 810 may be one of many x-ray images acquired in a continuous image stream. The x-ray image 810 may be an x-ray fluoroscopy image. In other embodiments, different types of x-ray images may be used. The x-ray image 810 provides the user with a view of a region of the patient anatomy through which the intravascular device 620 moved during an imaging procedure.

In some embodiments, the x-ray image 810 shown in the interface 800 is one of the x-ray images obtained by the x-ray imaging system 151 during the IVUS pullback procedure. In other embodiments, however, the x-ray image 810 may not be one of the x-ray images obtained during the pullback procedure. For example, the x-ray image 810 may be any suitable image acquired of the same region of the patient with a guidewire positioned within the same vessel imaged. In such an embodiment, the x-ray image 810 may be acquired from a similar angle as the x-ray images acquired during the procedure such that the shape, placement, orientation, and general appearance of the guidewire within the image 810 is similar to the pathway defined by the movement of the intravascular device 620 during the imaging procedure.

The system 100 may receive from the x-ray imaging system 151 a plurality of x-ray images. Some of these images may have been acquired as the pullback procedure was performed. In other words, some of the received x-ray images may have been received while the intravascular device 620 was acquiring IVUS images. However, some x-ray images received may not have been acquired during the pullback procedure. Rather, some may have been acquired before or after the pullback procedure.

In some embodiments, the x-ray image 810 may include a depiction of a radiopaque portion of the intravascular device 620, as shown in FIG. 8. Because the intravascular device 620 is constructed of radiopaque material, it may be visible in the image 810 acquired without contrast agent. For example, the portion of the intravascular device 620 that is visible in the x-ray image 810 can be the imaging assembly (e.g., transducer assembly) and/or radiopaque markers.

The image 810 may additionally depict one or more guidewires 890. The guidewire 890 may be constructed of radiopaque material such that it appears within the x-ray image 810. Because the guidewire 890 is positioned within the lumen to be imaged, it indicates the location of the vessel within the image 810. Any suitable number of guidewires 890 may be displayed within an x-ray image. For example, two guidewires 890 are shown within the image 810. Additional guidewires 890 may also be present.

The graphical user interface 800 may correspond to a display presented to the user of the system 100 during or after a pullback procedure. A pullback procedure may include an imaging procedure in which the intravascular device 620 is moved through the patient anatomy along the guidewire 890 within a lumen while the x-ray imaging system 151 simultaneously acquires fluoroscopy images of the same region of the patient anatomy without contrast agent inside the vessel. The marker 834 within the fluoroscopy image 810 may indicate a starting position of the intravascular device 620 at the beginning of the pullback procedure. For example, the marker 834 may identify the location along the guidewire 890 at which the first IVUS image was obtained during the pullback imaging procedure. Similarly, the marker 832 may indicate an ending position of the intravascular device 620 at the end of the pullback procedure. For example, the marker 832 may identify the location along the guidewire 890 at which the final IVUS image was obtained during the pullback imaging procedure. In this example, the pullback procedure may include moving the intravascular device 620 through the vessel from a location represented by the marker 834 to the location represented by the marker 832 while the device 620 acquires intravascular data. The system 100 can, e.g., automatically track movement of the radiopaque portion of the device 620 in the plurality of x-ray images acquired as the device 620 moves within the vessel. The intravascular device 620 may move from a distal location within a vessel to a proximal location, as described, or it may move in the opposite direction. For example, the marker 832 may indicate a starting location of the device 620 and the marker 834 may indicate an ending location.

A pathway 830 is also shown overlaid over the x-ray image 810. The pathway 830 may be similar to the pathway 630 described with reference to FIG. 6 or the pathway 740 described with reference to FIG. 7. For example, the pathway 830 may be determined and generated by the system 100 based on the locations of the radiopaque portion of the intravascular device 620 within the x-ray images acquired by the x-ray imaging system 151. The location of the device 620 may be determined by the system 100 using any above-mentioned image processing or deep learning techniques for each acquired x-ray image. These locations may together define the shape of the pathway 830 overlaid over the image 810. In this way, the length of the pathway 830 shown on the image 810 may correspond to the length along the vessel which was imaged by the intravascular device 620. Because the imaging device 620 moved along the guidewire 890, this pathway 830 is similar in shape to the corresponding section of the guidewire 890 representative of the imaged vessel as shown in FIG. 8. In some embodiments, the pathway 830 may not be shown. Indeed, any of the pathway 830 and the indicators 832 and 834 may not be displayed to the user within the graphical user interface 800. In addition, any of the pathway 830 and indicators 832 and 834 may appear differently than they appear in FIG. 8.

In some embodiments, the processor circuit of the system 100 may use some or a subset of the plurality of x-ray images received by the system during the pullback procedure to determine the path 830 of movement of the intravascular device 620 and/or co-registration of intravascular data to corresponding locations within the x-ray image 810. In some embodiments, all of the plurality of x-ray images received are used by the processor circuit to determine the path 830 and complete the coregistration. However, some of the x-ray images acquired may not depict the radiopaque portion of the device 620 or may have been acquired at a time when the device 620 was not acquiring IVUS images.

The process of coregistering intravascular data to locations within the x-ray image 810 along the guidewire 890 may include first co-registering the data to the pathway 830. For example, as explained with reference to FIG. 7, the plurality of IVUS images acquired by the device 620 may be coregistered to locations along the pathway 740. With reference to FIG. 8, using similar techniques, the acquired IVUS images may be coregistered to the pathway 830 shown in the interface 800. The pathway 830 is overlaid over the x-ray image 810 at the corresponding location as the guidewire 890. Because the pathway 830 is of the same shape as the guidewire 890 such that the pathway 830 aligns with the guidewire 890 throughout the length of imaged region of the vessel, the intravascular data that was coregistered to the pathway 830 may be additionally coregistered to the guidewire 890. As a result, the pathway 830 may be displayed or may not be. The indicator 882 and/or other bookmarks may be displayed with relation to the guidewire 890 without the pathway 830 being displayed.

The image 810 may include an indicator 882. The graphical user interface 800 additionally includes the IVUS image 840 displayed adjacent to the x-ray image 810. The indicator 882 may identify to the user of the system 100 the location along the guidewire 890 or pathway 830 at which the IVUS image 840 was obtained. Because the guidewire 890 is positioned within the imaged vessel, as the indicator 882 is displayed along the guidewire 890, it also identifies to the user the location along the imaged vessel at which the IVUS image 840 was acquired. Thus, even though the vessel cannot be directly visualized because the x-ray images were obtained without contrast, registration of the IVUS image to a corresponding location along the vessel is still possible because the guidewire 890 acts as the vessel. The indicator 882 is disposed along the guidewire 890, not the vessel, in the x-ray image 810 at a corresponding position of the IVUS image 840.

The indicator 882 may be of any suitable appearance and may be positioned at any suitable location relative to the guidewire 890. For example, the indicator 882 may be a single solid line, as shown. Alternatively, the indicator 882 may be of any suitable shape, profile, color, pattern, weight, or other appearance. The indicator 882 may be positioned overlaid on the guidewire 890 or the pathway 830 or may be positioned elsewhere. For example, the indicator 882 may be positioned adjacent to the guidewire 890 or the pathway 830. The indicator 882 may be positioned along an axis perpendicular to the guidewire 890 or the pathway 830 and spaced from the guidewire 890 or pathway 830 or positioned in any other location so as to indicate the location along the guidewire 890 or pathway 830 the location at which the IVUS image 840 was acquired. All or part of the indicator 882 may be positioned over the guidewire 890, adjacent to the guidewire 890, proximate to the guidewire 890, spaced from the guidewire 890, or combinations thereof. The indicator 882 may also be referred to as a marker, marking, identifier, scrubber, pointer, or any other suitable term.

Earlier coregistration systems required a roadmap x-ray image of a vessel that is obtained with contrast. The locations of coregistered IVUS images were displayed in the roadmap image relative to the contrast-filled vessel in these earlier systems. This required more time for the procedure because the contrast had to be introduced into the vessel and the x-ray image with contrast had to be taken. The present disclosure advantageously avoids the prolongation of the IVUS imaging procedure caused with the contrast and the potential patient discomfort associated with this delay and/or the contrast itself. Some patients may be sensitive to radiopaque contrast due to various conditions, such as impaired kidney function. Avoiding radiopaque contrast in such situations is clinically advantageous because it avoids risk of harm to the patient. In particular, the roadmap x-ray image 810 in the present disclosure does not have to be obtained with contrast or have a contrast-filled vessel. Rather, the roadmap x-ray image 810 can be obtained without contrast because the guidewire 890 that is positioned within the vessel is visible in the roadmap x-ray image. The marker or marking 882 is displayed relative to the guidewire 890, not the vessel.

The graphical user interface 800 additionally depicts an ILD 850. The IVUS images acquired with the device 620, may be used to create an ILD 850, shown adjacent to the IVUS image 840. In that regard, IVUS image 840 is a tomographic or radial cross-sectional view of the blood vessel. The ILD 850 provides a longitudinal cross-sectional view of the blood vessel. The ILD 850 can be a stack of the IVUS images acquired at various positions along the vessel, such that the longitudinal view of the ILD 850 is perpendicular to the radial cross-sectional view of the IVUS image 840. In such an embodiment, the ILD 850 may show the length of the vessel, whereas an individual IVUS image 840 is a single radial cross-sectional image at a given location along the length. In another embodiment, the ILD 850 may be a stack of the IVUS images acquired overtime during the imaging procedure and the length of the ILD 850 may represent time or duration of the imaging procedure. The ILD 850 may be generated and displayed in real time or near real time during the pullback procedure. As each additional IVUS image 840 is acquired by the device 620, it may be added to the ILD 850. For example, at a point in time during the pullback procedure, the ILD 850 shown in FIG. 8 may be partially complete. In some embodiments, the processor circuit may generate an illustration of a longitudinal view of the vessel being imaged based on the received IVUS images. For example, rather than displaying actual vessel image data as the ILD 850 does, the illustration may be a stylized version of the vessel, with e.g., continuous lines showing the lumen border and vessel border.

The ILD 850 may include an indicator 862. The indicator 862 may indicate to the user the location along the ILD 850 at which the IVUS image 840 was obtained. The indicator 862 may therefore correspond to the indicator 882. In some embodiments, the processor circuit may move the indicator 882 from one location along the guidewire 890 to another in response to a user input designating the new location. As the indicator 882 is moved to a different location, the indicator 862 may be moved to the corresponding location along the ILD 850 and the IVUS image acquired at the location may be displayed. In this way, the location at which the IVUS image shown in the graphical user interface 800 may be shown within the x-ray image 810 by the indicator 882 and within the ILD 850 by the indicator 862. Similarly, if the processor circuit moves the indicator 862 within the ILD 850 in response to a user input, the indicator 882 may move to the corresponding location along the guidewire 890 within the image 910 and the IVUS image acquired at that new location may be displayed.

The processor circuit may move the indicator 882 by any suitable method or in response to any type of user input. For example, the user may use a mouse to click on a location along the guidewire 890, may touch a location along the guidewire 890 using a touchscreen device, or may indicate the new location by any other way. In some embodiments, the user may select and drag the indicator 882 to a different location along the guidewire 890. Similarly, the user may move the indicator 862 to different locations along the ILD 850 by any of these methods as well. In some embodiments, the system 100 may step through the acquired IVUS images frame by frame in response to a user's selection of the arrows 892 and/or 894, for increased accuracy in frame identification. As an additional IVUS image is displayed, the scrubber 862 may move to the corresponding location along the ILD 850 and the marker 882 may move to its corresponding location within the x-ray image 810. In some embodiments, a selection of the arrows 892 and/or 894 may also direct the system 100 to display a different region of the ILD 850.

The indicator 862 displayed on the ILD 850 may be of any suitable appearance or positioned at any suitable location. For example, the indicator 862 may include a line extending perpendicularly across the ILD 850 as shown. The indicator 862 may include any suitable shape, such as a circle positioned at a central point along the line as shown. In other embodiments, the indicator may be of any pattern, weight, color, shape, profile, or any other appearance. The indicator 862 may be positioned over the ILD 850 as shown, or may be positioned next to the ILD 850 or positioned at any other suitable location so as to indicate the location along the ILD 850 at which the corresponding IVUS image shown was acquired.

The indicator 882 and/or the indicator 862 may alternatively be referred to by any suitable term, including but not limited to a scrubber, marker, marking, pointer, or by any other suitable term.

Figure 9:
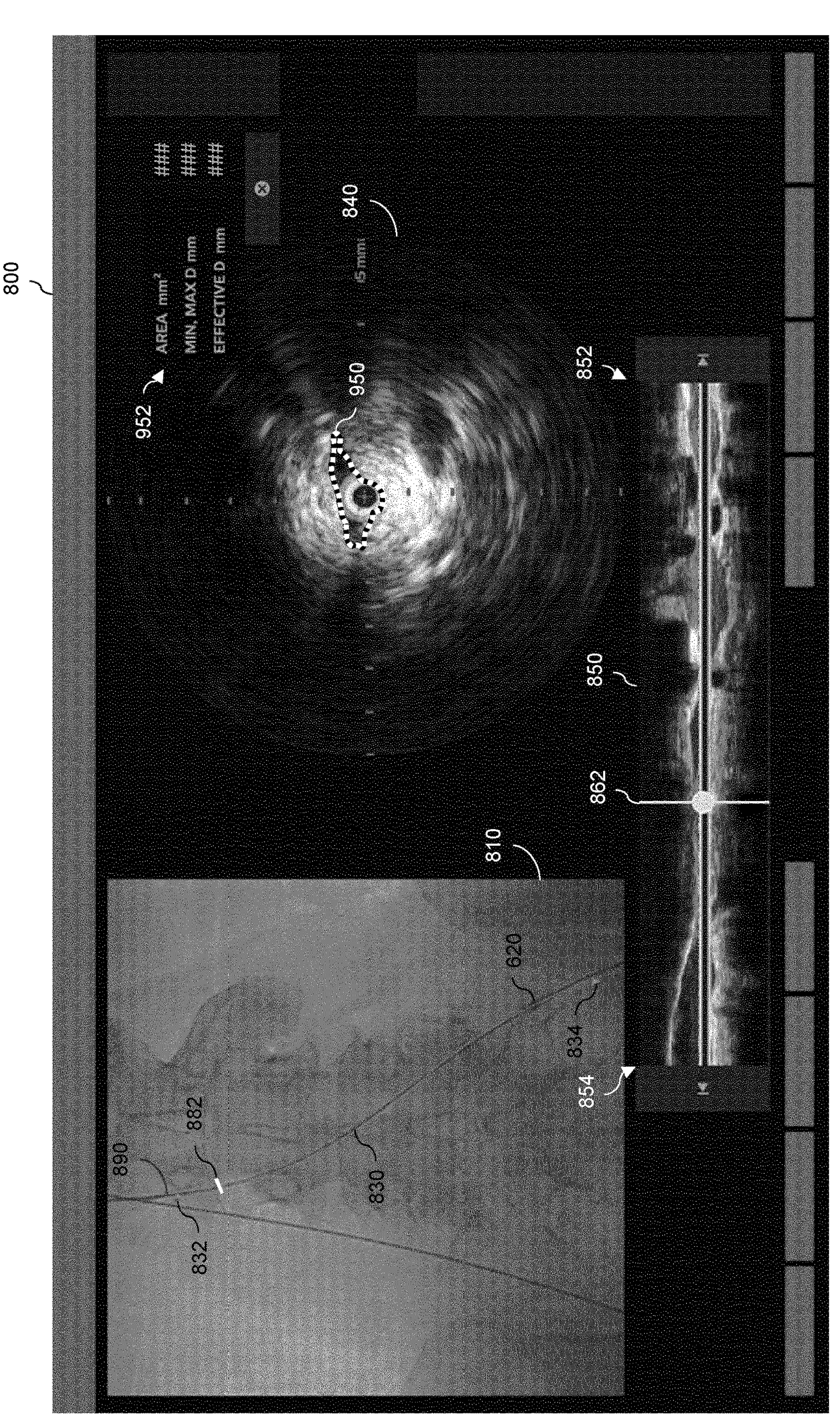
FIG. 9 is a diagrammatic view of a graphical user interface of FIG. 8 including measurements of the vessel depicted in the intravascular image.

FIG. 9 is a diagrammatic view of the graphical user interface 800 of FIG. 8 including measurements 952 of the vessel depicted in the intravascular image 840, as well as an outline 950 of the vessel lumen, according to aspects of the present disclosure.

The measurements 952 may display any suitable metrics to the user of the system 100. For example, the measurements 952 may include a cross sectional area of the lumen of the vessel imaged, the maximum diameter across the lumen of the vessel, the minimum diameter across the lumen of the vessel, an effective diameter of the lumen, and/or any other suitable measurements or metrics. In some embodiments, the measurements 952 may relate to the IVUS image 840 currently shown to the user within the interface 800. In other embodiments, the measurements 952 may also include measurements or metrics relating to other regions along the imaged vessel. For example, the measurements 952 may include metrics related to a proximal reference location (e.g., healthy vessel tissue proximal of a blood flow constriction), a distal reference location (e.g., healthy vessel tissue distal of a blood flow constriction), or a region of stenosis or vessel compression.

In some embodiments, the measurements 952 shown in FIG. 9 may be calculated and/or displayed to the user in response to a user input (e.g., selecting a button via mouse or touch screen input or otherwise providing a suitable user input). In some embodiments, the system 100 may automatically calculate some or all of the measurements 952 for each IVUS image acquired during an imaging procedure. In some embodiments, the system 100 may automatically display some or all of the respective measurements 952, when a corresponding IVUS image 840 is displayed in the screen display 800. The devices, systems, and methods described herein can include one or more features described in U.S. Publication No. 2019/0282182 and titled "Determination and Visualization of Anatomical Landmarks for Intraluminal Lesion Assessment and Treatment Planning," U.S. Publication No. 2019/0282211 and titled "Scoring Intravascular Lesions and Stent Deployment in Medical Intraluminal Ultrasound Imaging," U.S. Publication No. 2020/0029861 and titled "Intravascular Imaging Procedure-Specific Workflow Guidance and Associated Devices, Systems, and Methods," and U.S. Publication No. 2020/0029932 and titled "Systems, Devices, and Methods for Displaying Multiple Intraluminal Images in Luminal Assessment with Medical Imaging," and U.S. Publication No. 2019/0282199 and titled "Alternative Anatomical Borders of Blood Vessels and Associated Devices Systems and Methods," each of which is hereby incorporated by reference in its entirety.

The IVUS image 840 can also include an outline 950. In some embodiments, the outline 950 is a graphical or visual depiction related to the measurements 952. The outline 950 may be overlaid on the IVUS image 840, as shown in FIG. 9. The outline 950 may highlight the location and/or shape of the lumen of the vessel imaged. This may enable the user to more clearly identify the vessel lumen within each IVUS image displayed. However, the outline 950 may identify or highlight any other regions of interest or features of the vessel of the IVUS image 840 as well. For example, the outline 950 may be or include a line extending across the lumen of the vessel 840. This line may identify the location of a maximum diameter of the lumen within the image 840. A similar line may identify the location of the minimum diameter. The outline 950 may include any other suitable graphical representations such as lines, shapes, patterns, or any other elements to identify any suitable features of the image 840.

Figure 10:
FIG. 10 is a diagrammatic view of a graphical user interface displaying an intravascular image, a longitudinal view of the vessel, and an IVUS image preview, according to aspects of the present disclosure.

FIG. 10 is a diagrammatic view of a graphical user interface 800 displaying an intravascular image 840, the longitudinal view or ILD 850, and an IVUS image preview 1040, according to aspects of the present disclosure. The GUI 800 can also include the x-ray image 810. FIG. 10 includes the IVUS image preview 1040 at a position along the ILD 850 shown by an indicator 1062 and with overlaid measurements 1052 and an outline 1050. In some embodiments, an indicator 1072 along the pathway 830 or guidewire 890 may also be included indicating the location of the preview image 1040 within the x-ray image 810.

In some instances, either during an IVUS imaging procedure or after the IVUS imaging procedure is complete, the user of the system 100 may wish to view a different IVUS image acquired than the IVUS image 840 displayed in the screen display 800. However, the user may not want to move the location of the scrubber 862 or change the IVUS image 840. In some embodiments in which an x-ray image 810 is displayed, the user may also not wish to move the location of the indicator 882 within the x-ray image 810. For example, the IVUS image 840, and the corresponding locations 862, 882 may be a region of the vessel the user has confirmed is of interest. The user may want to explore another region of the vessel that is not yet confirmed to be of interest, without changing the position of the scrubber 862 or the marker 882 identifying the location that has been confirmed to be of interest. The system 100 may allow a user to retrieve a temporary preview 1040 of other IVUS images as shown in FIG. 10. This may allow a user of the system 100 to quickly and easily compare the currently displayed IVUS image 840 and any of its corresponding measurements with another IVUS image within the set and its measurements.

To show a preview image, in response to an input from the user, the system 100 may begin or enter a preview mode, or, the processor circuit 134 may begin or enter a preview mode. To allow a user to temporarily view a different IVUS image, the system 100 may display a preview image 1040 in a preview window at its corresponding location along the ILD 850. The preview image 1040 may alternatively be referred to as a popup image or popup, a thumbnail image or thumbnail, or any other applicable term. The preview 1040 may be displayed at its corresponding location by being placed at a location adjacent to the ILD 850. For example, the preview 1040 may be positioned above the ILD 850, below the ILD 850, or to the left or right of the ILD 850. The preview 1040 may fully or partially cover, obscure, or be overlaid over part of the IVUS image 840 or the x-ray image 810, such that all or portion of the IVUS image 840 or the x-ray image 810 is shown in the background. In some embodiments, the location of the preview 1040 may not cover the IVUS image 840 or the x-ray image 810 and the preview 1040, the IVUS image 840, and the x-ray image 810 may all be viewed in their entirety. In some embodiments, the size of the images 810 and 840 and the preview 1040 may be adjusted so that one image does not overlap another. For example, the size of the IVUS image 840 or x-ray image 810 may be temporarily reduced or the size of the preview 1040 may be reduced when the preview 1040 is displayed. The preview image 1040 may be larger or smaller than the IVUS image 840 or may be the same size. The preview image 1040 may be larger or smaller than the x-ray image 810 or may be the same size. The IVUS image 840 may be larger or smaller than the x-ray image 810 or may be the same size. The positions of the preview 1040, the IVUS image 840, and/or the x-ray image 810 may also be adjusted. Any of these images may be displayed at any location within the screen display 800.

The location of the preview image 1040 along the ILD 850 may be marked by an indicator 1062. This indicator 1062 may serve a similar purpose to the indicator 862 in that it identifies the location at which the preview IVUS image 1040 was acquired with respect to other IVUS images constituting the ILD 850. Like the indicator 862, the indicator 1062 may be of any suitable appearance. In some embodiments, the appearance of the indicator 1062 may differ from the appearance of the indicator 862. This difference may convey to the user that the location of the indicator 862 within the ILD 850 corresponds to the location of the IVUS image 840 while the location of the indicator 1062 corresponds to the location of the preview image 1040.

In one embodiment, the user may use a mouse to provide user inputs to the system 100 associated with the indicators 862 and/or 1062. For example, the user may move the location of the indicator 862 by selecting the indicator 862, moving the cursor to a different location along the ILD 850, and releasing the indicator 862. As explained with reference to FIG. 8, this may display a new IVUS image 840 and move the indicator 882 in the x-ray image 810 to the corresponding location. The user may alternatively simply select a location along the ILD 850 to cause the indicator 862 to move to that location and cause the related images to update.

The user of the system 100 may indicate to the system to display a preview image 1040 by any suitable means. For example, a user input may include a selection or actuation of a button, such as a keyboard key or a mouse button. Selection or actuation may include a touch from a user on a touch screen device including a short press, a long press, a press of lesser or greater pressure, or any other type of touch or gesture, a voice command, or any other user input. In some embodiments, to view a preview image 1040, the user may move the cursor to a different location along the ILD 850. The system 100 may track the movement of the cursor along the ILD 850 to determine whether a preview image 1040 is to be displayed. For example, the system may monitor the location of the cursor and a duration of time the cursor remains in a given region. The system 100 may specify a length along the ILD 850 in one or multiple directions of the cursor. For example, the system 100 may define a region around the cursor by the number of IVUS images on either side of the section of the ILD relating to one image. After a user moves the cursor to a location along the ILD 850 other than the location of the indicator 862, the system 100 may define a region around the cursor as, for example, 5 images distal, and 5 images proximal to the location of the cursor. The system 100 may then also monitor the amount of time, or duration of time, that the user leaves the cursor within that region. This threshold duration may be 1 second, 2 seconds, or more, or any suitable amount of time. After this predetermined duration of time has passed, if the user has not moved the cursor outside the predefined region, the system 100 may display the preview 1040 of an IVUS image corresponding to the location along the ILD 850 where the cursor is located. In some embodiments, the user of the system 100 may adjust either of these thresholds. For example, the user may adjust the number of IVUS image frames on either side of the cursor that may define a region. The region may also be defined by other units, such as pixels, units of length, such as mm, units of time, such as seconds, or by any other units. The user may also adjust the length of time after which a preview image 1040 is displayed after the cursor remains within the predetermined region of the ILD 850. As an example, if the ILD 850 is displayed to the user horizontally, a threshold region or threshold positioning of a cursor or similar indicator may be defined as a distance to the right or left of the cursor or indicator. However, if the ILD is positioned vertically, the region may be a distance above or below the cursor or indicator.

After the preview image 1040 is displayed to the user at one location along the ILD 850, the system 100 may no longer require the location of the cursor to satisfy the two thresholds (e.g., location within a region and time in that region). Rather, as the user moves the cursor to different locations along the ILD 850, the system 100 may move the preview 1040 along with the cursor and may continuously update the preview image 1040 and/or the measurements 1052 and outline 1050 accordingly.

While the preview 1040 is displayed at a location along the ILD 850, if the user wishes to move the indicator 862 to the location of the preview 1040, the user may click on the preview 1040, the indicator 1062, and/or locations in the GUI 800 aligned with the preview 1040 and/or the indicator 1062. The indicator 862 may then move to the new selected location (the location of the indicator 1062) along the ILD 850. The IVUS image 840 may be replaced with the IVUS image in the preview 1040 and the preview 1040 may no longer be displayed. The indicator 882 may also move to a corresponding location along the guidewire 890 or pathway 830 in the x-ray image 810. The user may also indicate to the system 100 to move the indicator 862 to the location of the preview 1040 and update the IVUS image 840 by any other suitable methods.

In some embodiments, when no preview image 1040 is shown, the user may select a button within the interface 800 to show the preview 1040. After the button is selected, the system 100 may begin to display a preview IVUS image 1040 at the location along the ILD 850 nearest the cursor at the time the button was pressed. As the cursor is moved to different locations along the ILD 850, the preview IVUS image 1040 and its corresponding measurements 1050 and outline 1050 may be continuously updated along with the location corresponding to the location of the cursor. A button may also be pressed to remove the preview 1040 from the display. Selecting a button within the interface 800 may advantageously save the user time, e.g., to quickly skim through many preview images, rather than waiting for a threshold amount of time to pass before the preview image is activated or providing a particular kind of user input to activate the preview image (e.g., a long press).

In other embodiments, the user may select a key from a keyboard or some other input device to cause the system 100 to display a preview image 1040. For example, the system 100 may display a preview image 1040 at a location along the ILD 850 closest to the location of the cursor when the key is depressed. In some examples, the system 100 may only display the preview image 1040 when the key is held and may stop displaying the preview image 1040 when the key is released or when there is a cessation of the user input, whatever the type of input may be. While the key is depressed, the user may move the cursor to show continuously updating preview images 1040 and corresponding measurements 1052 and outlines 1050 corresponding to the changing locations. The user may indicate to the system 100 to move the indicator 862 to the location of the preview 1040 by selecting the location along the ILD 850 as described, or by any other method.

In some embodiments, the preview 1040 may be removed from the interface 800 by a number of methods of input, or may be removed without any input from the user. For example, the user may select a key from a keyboard, such as an escape key, or by selecting a different button on a mouse, such as a right-click stroke. In some embodiments, the system 100 may also monitor the location of the cursor and the amount of time the cursor stays within a region. For example, if a user moves the cursor away from the ILD 850, the preview 1040 may be removed. In some embodiments, if the user moves the cursor away from the ILD 850 for a predetermined amount of time, the preview 1040 may be removed. In some embodiments, the user may select or click on any location other than on the ILD 850 to remove the preview 1040. Other suitable methods of removing the preview 1040 may also be used.

In some embodiments, other input devices may be used in connection with the system 100. For example, an input device may include a touch screen device. In such an embodiment, the user may touch various locations along the ILD 850 and cause the indicator 862 to move to those locations. In some embodiments, the user may move the indicator 862 by touching the location on the ILD 850 for a predetermined amount of time. For example, by touching a location for at least 1 second, the indicator 862 may move to the new location and the corresponding IVUS image 840 and indicator 882 may be updated as described. In some embodiments, the processor circuit may also move the indicator 862 to a new location and display the corresponding IVUS image of that location in response to a touch from the user of varied pressure. For example, a touch with greater pressure along the ILD 850 may move the indicator 862 and show a new IVUS image. Whereas, a touch of lesser pressure may display a preview IVUS image 1040.

In some embodiments, if a user wants to view a preview image 1040, the user may provide one kind of user input (e.g., one of a long press or a short press) at a location along the ILD 850 to activate the preview image 1040. Once the preview image is activated and as the user moves their finger along the ILD 850, the location of the preview 1040 and the IVUS image 1040 with its corresponding measurements 1052 and outline 1050 may continuously update as previously described. In such an embodiment, the system 100 may move the scrubber 862 in response to a different kind of user input (e.g., the other of the long press or the short press) at a location along the ILD.

In an embodiment in which a touch screen is used as in input device, the user inputs may also include selecting any appropriate buttons within the interface 800.

It is contemplated that other devices of input or interaction may be used in connection with the 100 to allow a user to input any of the previously described signals or commands to the system. Such input devices may include any suitable touch screen devices, devices with physical buttons, or any other suitable input device.

The preview image 1040 may include the measurements 1052 and/or an outline 1050 or other graphical representation. The measurements 1052 may include any of the measurements 952 of FIG. 9. However, the measurements 1052 may relate to the IVUS image shown in the preview 1040. The measurements 1052 may be displayed overlaid over the preview image 1040 as shown or may be positioned at other locations. In some embodiments, the text and/or metrics of the measurements 1052 may be of a different color or style than the measurements 952 so as to easily distinguish the two sets of measurements. The outline 1050 may be similar to the outline 950 in that it may convey or highlight any of the same features of the preview image 1040 as the outline 950 highlighted within the image 840. Similar to the difference in appearance of the measurements 952 and measurements 1052, the outline 1050 may be of a different appearance than the outline 950. For example, the outline 1050 and/or the outline 950 may be of any suitable differing colors, patterns, profiles, shapes, or other appearance. The measurements or metrics 1052 may include textual descriptions or numeric values relating to an area, cross-sectional area, length, distance, diameter, circumference, perimeter, or any other metric.

It is noted that any of the user inputs described with reference to FIG. 10 regarding the initiation of the display of the preview image 1040 or ceasing to display the preview image 1040 may be recognized by the system 100. For example, the system 100 may display the preview image 1040 in response to a pointer device, such as a mouse, being positioned within a threshold region for a threshold time, in response to a user selection of a button within the interface 800, in response to a user selection of a button or similar feature on a keyboard, mouse or any other input device, in response to a touch of a screen, or any other user input. The system 100 may stop displaying the preview 1040 in response to any of these same user inputs as well. In some embodiments, a user of the system 100 may select or customize which user inputs correspond to which commands to the system 100 and may select any of these embodiments. In some embodiments, the system 100 may only display or stop displaying the preview 1040 in response to one of the user inputs described. The system can also receive any suitable user input to activate or deactivate completely the system providing the preview image.

Figures 11, 12:
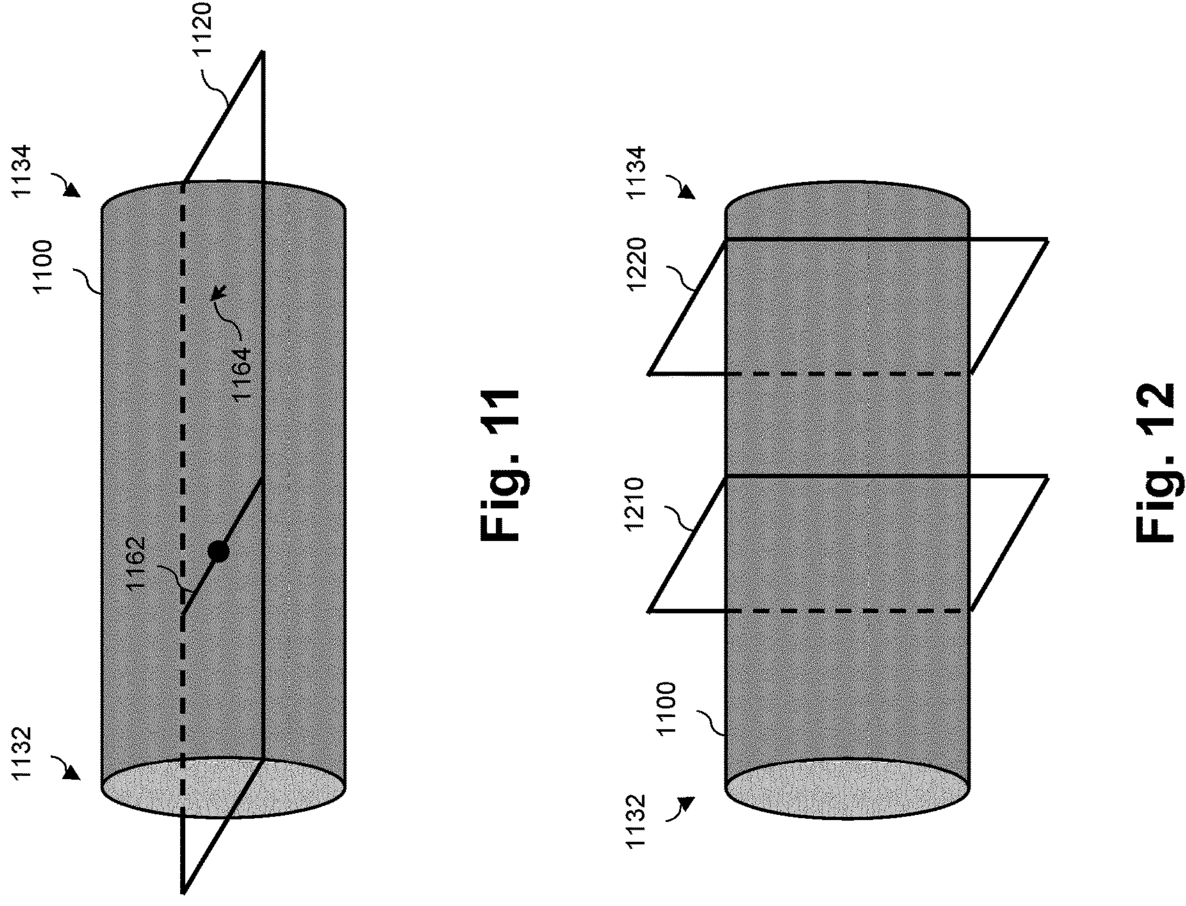
FIG. 11 is a diagrammatic perspective view of a representative body lumen, according to aspects of the present disclosure.
FIG. 12 is a diagrammatic perspective view of a representative body lumen, according to aspects of the present disclosure.

FIG. 11 is a diagrammatic perspective view of a representative lumen 1100, according to aspects of the present disclosure. FIG. 11 includes various graphical representations including a longitudinal plane 1120, an indicator 1162, and a representative cursor 1164. FIG. 11 further describes the relationship of the ILD 850 to the section of the patient vessel imaged and various locations along the ILD 850 or vessel. FIG. 11 will be described in connection with FIG. 12, which is a diagrammatic perspective view of a representative lumen 1100, according to aspects of the present disclosure. FIG. 12 additionally depicts an image frame 1210 and an image frame 1220 relating to IVUS images or other data acquired at locations along the imaged vessel.

The body lumen 1100 shown in FIGS. 11 and 12 is represented as a cylindrical shape for the purposes of explanation. The patient vessel and/or vessel lumen imaged during a IVUS imaging procedure may have a similar shape in some instances. In other instances, the shape of the patient vessel or vessel lumen may be different. The lumen 1100 shown may represent a section of a patient blood vessel or any other imaged lumen. For example, the region 1134 may correspond to a distal region within the lumen 1100, or the distal most location at which an IVUS image was acquired during an imaging procedure. Referring to FIG. 8, region 1134 may correspond to a region similar to region 834. Similarly, the region 1132 may correspond to a proximal region within the lumen 1100, or the proximal most location at which an IVUS image was acquired during an imaging procedure. Referring to FIG. 8, region 1132 may correspond to a region similar to region 832.

FIG. 11 depicts a longitudinal plane 1120. The longitudinal plane 1120 may be representative of an ILD corresponding to the lumen 1100. For example, the lumen 1100 may also be representative of a stack of all the IVUS images acquired during an imaging procedure. Aspects of these IVUS images may be combined to produce an ILD of the section of the vessel. This ILD, as shown by the longitudinal plane 1120 may provide the user with a representative longitudinal cross-section of the imaged portion of the vessel.

The indicator 1162 shown within the longitudinal plane 1120 may be similar to the indicator 862 of FIG. 8. A user may select a location along the ILD and a corresponding IVUS image may be displayed (e.g., IVUS image 840 in the GUI 800). Referring to FIG. 8, this location may be shown by the indicator 862. The indicator 1162 may illustrate where along the imaged vessel the IVUS image was acquired. The image frame 1210 shown in FIG. 12 may be illustrative of the IVUS image corresponding to the location along the vessel shown by the indicator 1162. Any IVUS image acquired or displayed by the system 100 may be described as a cross-sectional image of the vessel, a cross-sectional radial image, circumferential image, or tomographic image.

Similarly, as described with reference to FIG. 10, the user may use a cursor to select new locations along the ILD or signal to the system 100 to display a preview image (e.g., preview 1040 of the GUI 800). A representative cursor is shown in FIG. 11 as well. This cursor 1164 may be moved to various locations along the ILD as shown by the panel 1120. As the cursor is moved along the ILD, its location corresponds to different locations along the imaged vessel 1100. Each of these different locations may correspond to an IVUS image acquired at that location. For example, the location of the cursor 1164 along the lumen 1100 or ILD may have a corresponding IVUS image as shown by the frame 1220 of FIG. 12. At this location, if the user indicated to the system 100 to display a preview image similar to the preview image 1040 of FIG. 10, the IVUS image corresponding to frame 1220 would be displayed as a preview. Alternatively, the user may indicate to move the indicator 1162 to the location of the cursor 1164 by any of the procedures described and the image 1220 may appear within the graphical user interface as the primary IVUS image 840 (FIG. 10). It will be appreciated that any number of IVUS images may constitute the lumen 1100 or ILD such that as the cursor 1164 is moved to any location along the panel 1120 shown, a different IVUS image may be displayed corresponding to the current location of the cursor 1164.

Although the frames 1210 and 1220 shown in FIG. 12 are of a rectangular shape, it is noted that they may represent IVUS images of a circular shape. The frames 1210 and 1220 may be of any shape and the graphical representations of FIGS. 11 and 12 may or may not be displayed to the user. The frames 1210 and 1220 as well as any other frames or IVUS images may thus be arranged in a stacked arrangement.

Figure 13:
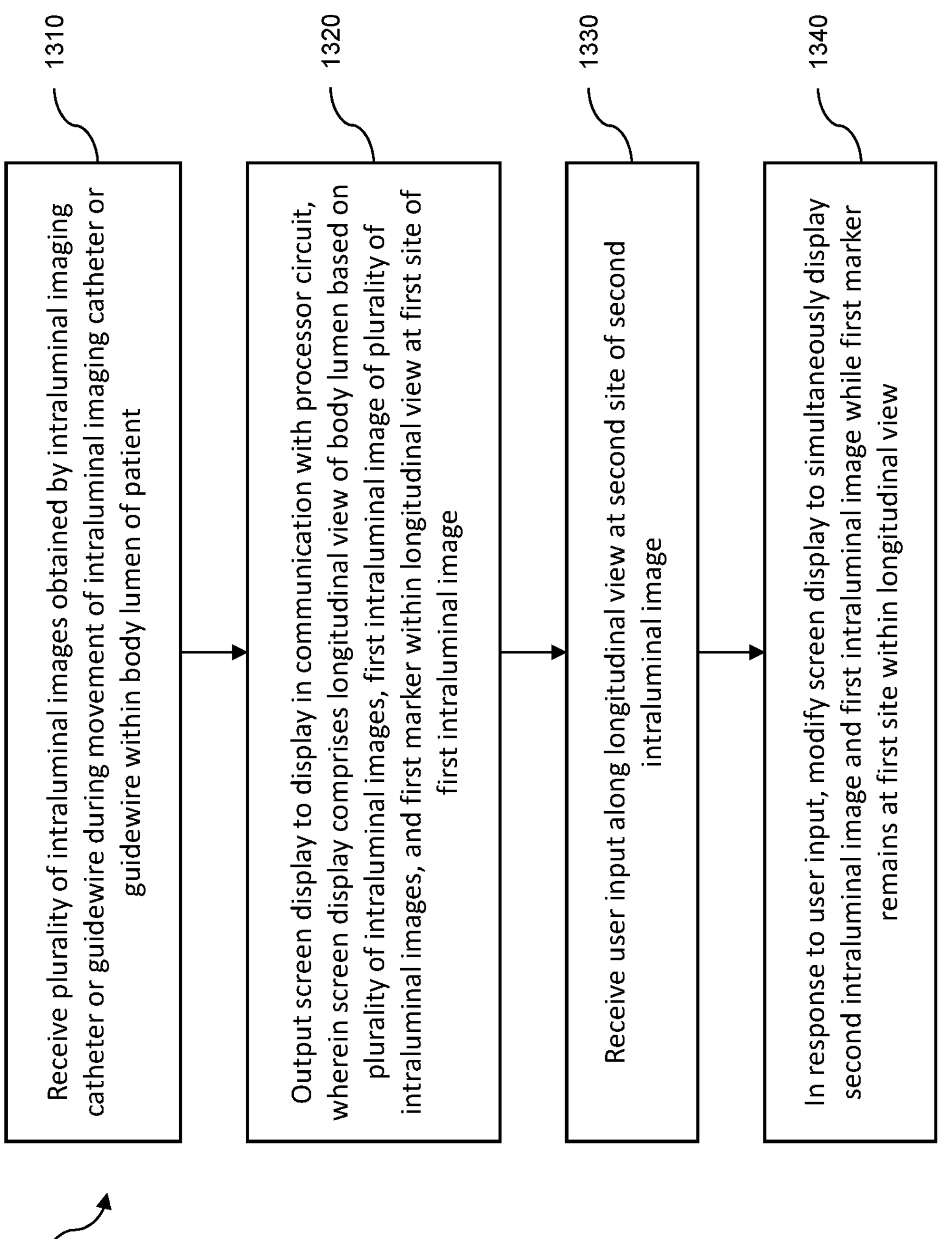
FIG. 13 is a flow diagram for a method for previewing an IVUS image, according to aspects of the present disclosure.

FIG. 13 is a flow diagram for a method of displaying a preview IVUS image, according to aspects of the present disclosure. As illustrated, the method 1300 includes a number of enumerated steps, but embodiments of the method 1300 may include additional steps before, after, or in between the enumerated steps. In some embodiments, one or more of the enumerated steps may be omitted, performed in a different order, or performed concurrently. The steps of the method 1300 can be carried out by any suitable component within the system 100 and all steps need not be carried out by the same component. In some embodiments, one or more steps of the methods 1300 can be performed by, or at the direction of, a processor circuit of the system 100 (e.g., the processor circuit 510 of FIG. 5), including, e.g., the processor 560 or any other component.

At step 1310, the method 1300 includes receiving a plurality of intraluminal images obtained by the intraluminal imaging catheter or guidewire during movement of the intraluminal imaging catheter or guidewire within a body lumen of a patient. For example, step 1310 can include receiving a plurality of IVUS images obtained by the IVUS imaging catheter or guidewire during movement of the IVUS imaging catheter within a blood vessel of a patient.

At step 1320, the method 1300 includes outputting a screen display to a display in communication with the processor circuit. In some embodiments, the screen display comprises a longitudinal view of the body lumen based on the plurality of intraluminal images; a first intraluminal image of the plurality of intraluminal images; and a first marker within the longitudinal view at a first site of the first intraluminal image. For example, step 1320 can include outputting a screen display to a display in communication with the processor circuit. In some embodiments, the first screen display comprises a longitudinal view of the blood vessel comprising a stack of the plurality of IVUS images; a first IVUS image of the plurality of IVUS images; and a marker within the longitudinal view at a first site of the first IVUS image.

At step 1330, the method 1300 includes receiving a user input along the longitudinal view at a second site of a second intraluminal image. For example, step 1330 can include receiving a user input along the longitudinal view at a second site of a second IVUS image The user input may include positioning of a selection tool at second site without actuation of the selection tool.

At step 1340, the method 1300 includes, in response to the user input, modifying the screen display to simultaneously display the second intraluminal image and the first intraluminal image while the first marker remains at the first site within the longitudinal view. For example, the step 1340 can include, in response to the user input, modifying the screen display to display the second IVUS image. For example, the second IVUS image may be overlaid on the screen display proximate to the second site along the longitudinal view, and simultaneously as the first IVUS image such that the marker remains at the first site within the longitudinal view.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system, comprising:

a processor circuit configured for communication with an extraluminal imaging device and an intraluminal imaging catheter or guidewire, wherein the processor circuit is configured to:

receive a plurality of intraluminal images obtained by the intraluminal imaging catheter or guidewire during movement of the intraluminal imaging catheter or guidewire within a body lumen of a patient;

receive a plurality of first extraluminal images obtained by the extraluminal imaging device during the movement of the intraluminal imaging catheter or guidewire, wherein the plurality of first extraluminal images are obtained without a contrast agent within the body lumen, and wherein the plurality of first extraluminal images show a radiopaque portion of the intraluminal imaging catheter;

co-register the plurality of intraluminal images to corresponding positions along the body lumen based on the plurality of first extraluminal images;

output a screen display to a display in communication with the processor circuit, wherein the screen display comprises:

a longitudinal view of the body lumen based on the plurality of intraluminal images;

a primary intraluminal image area comprising a first intraluminal image of the plurality of intraluminal images, wherein the first intraluminal image depicts a first location along the body lumen;

a first marker indicating the first location within the longitudinal view;

an extraluminal image area comprising a second extraluminal image; and a second marker indicating the first location within the second extraluminal image;

receive a user input configured to identify a second intraluminal image of the plurality of intraluminal images, wherein the second intraluminal image depicts a second location along the body lumen, wherein the user input is received at the second location within the longitudinal view; and in response to the user input, add a preview intraluminal image window to the screen display such that the second intraluminal image is shown within the preview intraluminal image window while the first intraluminal image remains displayed within the primary intraluminal image area and the first marker remains at the first location within the longitudinal view, wherein, before the user input is received, the screen display does not include the preview intraluminal image window, wherein each of the longitudinal view, the primary intraluminal image area, the user input, and the preview intraluminal image window is associated with the plurality of intraluminal images.

2. The system of claim 1, wherein the longitudinal view of the body lumen comprises a stack of the plurality of intraluminal images.

3. The system of claim 1, wherein the user input comprises positioning a selection tool at the second location within the longitudinal view without actuation of the selection tool.

4. The system of claim 3, wherein the processor circuit is configured to:

receive an actuation of the selection tool;

in response to the actuation, modify the screen display to:

replace the first intraluminal image in the primary intraluminal image area with the second intraluminal image; and move the first marker to the second location within the longitudinal view.

5. The system of claim 4, wherein, to receive the user input, the processor circuit is configured to:

compare the positioning of the selection tool at the second location within the longitudinal view to a threshold positioning; and detect the user input based on the comparison.

6. The system of claim 4, wherein, to receive the user input, the processor circuit is configured to:

compare a duration of the positioning of the selection tool at the second location within the longitudinal view to a threshold duration; and detect the user input based on the comparison.

7. The system of claim 1, wherein, in response to the user input, the processor circuit is configured to modify the screen display to include a third marker at the second location within the longitudinal view while the first marker remains at the first location within the longitudinal view.

8. The system of claim 1, wherein a size of the preview intraluminal image window is smaller than the size of the primary intraluminal image area.

9. The system of claim 1, wherein the processor circuit is configured to determine a location of the preview intraluminal image window within the screen display based on the user input.

10. The system of claim 9, wherein, in response to the user input being received at the second location within the longitudinal view, the location of the preview intraluminal image window is proximate to the second location within the longitudinal view.

11. The system of claim 1, wherein the preview intraluminal image window is overlaid over at least a portion of the primary intraluminal image area.

12. The system of claim 11, wherein the second intraluminal image in the preview intraluminal image window obscures at least a portion of the first intraluminal image in the primary intraluminal image area.

13. The system of claim 12, wherein the second intraluminal image in the preview intraluminal image window obscures at least a portion of the second extraluminal image in the extraluminal image area.

14. The system of claim 1, wherein the preview intraluminal image window is overlaid over at least a portion of the extraluminal image area.

15. The system of claim 1, wherein the second extraluminal image is one of the plurality of first extraluminal images.

16. The system of claim 1, wherein, in response to the user input, the processor circuit is configured to modify the screen display to provide a third marker at the second location within the second extraluminal image while the second marker remains at the first location within the second extraluminal image.

17. The system of claim 1, wherein, in response to the user input, the processor circuit is configured to determine a metric of the body lumen corresponding to the second intraluminal image, wherein the preview intraluminal image window comprises a graphical representation of the metric.

18. The system of claim 1, wherein the processor circuit is configured to:

determine a cessation of the user input; and in response to the cessation of the user input, modify the screen display to remove the preview intraluminal image window.

19. The system of claim 1, further comprising the intraluminal imaging catheter or guidewire, wherein the intraluminal imaging catheter or guidewire comprises an intravascular imaging catheter configured for intravascular ultrasound (IVUS) or optical coherence tomography (OCT), wherein the plurality of intraluminal images comprises a plurality of intravascular images, wherein the body lumen comprises a blood vessel of the patient.

* * * * *